United States Patent [19]

Berg et al.

[11] Patent Number: 5,387,977
[45] Date of Patent: Feb. 7, 1995

[54] MULTIANGULAR COLOR MEASURING APPARATUS

[75] Inventors: Bernard J. Berg, Kentwood; Thomas J. Boes, Grandville; Mark A. Cargill, Belding, all of Mich.

[73] Assignee: X-Rite, Incorporated, Grandville, Mich.

[21] Appl. No.: 754,905

[22] Filed: Sep. 4, 1991

[51] Int. Cl.⁶ .................................................. G01N 21/25
[52] U.S. Cl. ....................................... 356/407; 356/406; 250/227.3
[58] Field of Search ............... 356/402, 407, 446, 328, 356/405, 406; 250/227.24, 227.3; 364/526

[56] References Cited

U.S. PATENT DOCUMENTS

| | | |
|---|---|---|
| 2,287,322 | 6/1942 | Nelson . |
| 3,244,062 | 4/1966 | Sweet . |
| 3,363,108 | 1/1968 | Spurr et al. . |
| 3,389,265 | 6/1968 | Schreckendgust ............ 250/226 |
| 3,549,264 | 12/1970 | Christie ........................... 356/446 |

(List continued on next page.)

OTHER PUBLICATIONS

Datacolor AG, "Metallics-Visions are now measureable", date unknown.
Coatings Magazine, "Many Developments in Equipment for Color Matching," date unknown. only p. 102.
Rodrigues, "Measurement of Metallic & Pearlescent Colors", Sep. 4, 1990, pp. 1-12.
Letter dated Dec. 8, 1989 regarding Paint Show '89 by BYK-Chemie USA.
Celio, "Spectrophotometric Instrument for Graphic Arts," pp. 583-603, journal and date unknown.
Gretag, brochure of 6 pages re Gretag SPM 100 Spectrophotometer, date unknown.
D. R. Lange, brochure of 8 pages regarding reflectometer, date unknown.
BYK-Gardner, brochure of 4 pages regarding gloss measuring, date unknown.
Macbeth, Division of Kollmorgen, brochure of two pages re Goniospectrophotometer, date unknown.
Datacolor, brochure of 2 pages regarding GK 111 color measuring, date unknown.
Datacolor, brochure of 2 pages regarding MMK 111 color measuring, date unknown.

*Primary Examiner*—Vincent P. McGraw
*Assistant Examiner*—K. P. Hantis
*Attorney, Agent, or Firm*—Varnum, Riddering, Schmidt & Howlett

[57] ABSTRACT

A spectrophotometer apparatus (200) is adapted to provide spectral reflectance measurements of an object sample (236) under test, particularly optical characteristics of colored surfaces comprising metallic or pearlescent particles. The apparatus (200) comprises a source light (226) and a reflection optics assembly. Signals representative of reflected light are analyzed and data is generated representative of the spectral response characteristics of the object sample (236). The apparatus (200) employs a plurality of fiber optic bundles (248, 250, 252) for receiving light reflected from the object sample (236), with each of the fiber optic bundles (248, 250, 252) being positioned at one of a corresponding plurality of fixed angles different from the angle of illumination of the source light (226). Reflectance is measured at each angle by sequential switching such that light is impaired from being received by all but a subset of the plurality of multiple angles. Light received from the fiber optic bundles is transferred to a single array of integral interference-filter/photodiode devices (284) which modulate the light and determine the spectral characteristics thereof. With the use of fiber optic devices, a single source of illumination and a single optical detector arrangement, the spectrophotometer apparatus (200) is employed within an optimally small packaging configuration, and the apparatus (200) can be maintained in a portable mode while maintaining relatively high accuracy and repeatability.

19 Claims, 9 Drawing Sheets

U.S. PATENT DOCUMENTS

| | | | |
|---|---|---|---|
| 3,690,771 | 9/1972 | Armstrong, Jr. et al. | |
| 3,712,745 | 1/1973 | Armstrong, Jr. et al. | |
| 3,756,721 | 9/1973 | Williams. | |
| 3,756,726 | 9/1973 | Astheimer. | |
| 3,806,256 | 4/1974 | Ishak. | |
| 3,814,932 | 6/1974 | Anati et al. | |
| 3,817,628 | 6/1974 | Adams. | |
| 3,846,024 | 11/1974 | Turner. | |
| 3,885,878 | 5/1975 | Ishak. | |
| 3,916,168 | 10/1975 | McCarty et al. | |
| 3,992,101 | 11/1976 | Dapper et al. | |
| 3,999,864 | 12/1976 | Mutter. | |
| 4,003,660 | 1/1977 | Christie, Jr. et al. | |
| 4,061,428 | 12/1977 | Amano et al. | |
| 4,072,426 | 2/1978 | Horn. | |
| 4,165,180 | 8/1979 | Failes | 356/310 |
| 4,218,144 | 8/1980 | Whitehouse et al. | 356/446 |
| 4,232,219 | 11/1980 | Yamamoto et al. | 250/227 |
| 4,412,744 | 11/1983 | Lee et al. | 356/319 |
| 4,417,818 | 11/1983 | Weisner | 356/404 |
| 4,449,821 | 5/1984 | Lee | 356/319 |
| 4,467,438 | 8/1984 | Zerlaut et al. | 364/525 |
| 4,479,718 | 10/1984 | Alman | 356/405 |
| 4,527,898 | 7/1985 | Stapleton | 356/446 |
| 4,572,672 | 2/1986 | Orchard et al. | 356/446 |
| 4,583,858 | 4/1986 | Lebling et al. | 356/405 |
| 4,591,978 | 5/1986 | Peterson et al. | 364/200 |
| 4,652,913 | 3/1987 | Saitoh et al. | 358/75 |
| 4,659,933 | 4/1987 | Anthon | 280/372 |
| 4,666,309 | 5/1987 | Barry et al. | 356/446 |
| 4,681,454 | 7/1987 | Breemer | 356/402 |
| 4,711,580 | 12/1987 | Venable | 356/406 |
| 4,814,597 | 3/1989 | Kruger et al. | 250/205 |
| 4,917,495 | 4/1990 | Steenhoek | 356/328 |
| 5,015,098 | 5/1991 | Berg et al. | 356/402 |
| 5,087,937 | 2/1992 | Frick et al. | 355/1 |
| 5,118,183 | 6/1992 | Cargill et al. | 356/73 |

MULTIANGULAR COLOR MEASURING APPARATUS

BACKGROUND OF THE INVENTION

1. Field of the Invention

The invention relates to apparatus and methods associated with color measurement and analysis technology and, more particularly, apparatus and methods for measuring color characteristics of object samples comprising metallic and/or pearlescent particles.

2. Description of Related Art

It is well-known that the term "color" as applied to electromagnetic radiation represents in part the relative energy distribution of radiation within the visible spectrum. That is, light providing a stimulus to the human eye, and having a particular energy distribution, may be perceived as a substantially different color than light of another energy distribution. Concepts relating to the characteristics of color and light waves are the subject of numerous well-known texts, such as *Principles of Color Technology*, Meyer, Jr. and Saltzman (Wiley 1966) and *The Measurement of Appearance*, Hunter and Harold (Wiley 2nd Ed. 1987).

In recent years, the capability of maintaining the "quality of color" has been of significant importance in various industries, such as, for example, the fields of graphic arts, photography and color film processing. In addition, maintaining the quality of color is of significant importance in manufacturing industries producing objects having colored surfaces. For example, the automotive industry requires relatively high accuracy in measuring color characteristics of painted surfaces for purposes of maintaining color quality and repeatability for manufacture and repair of pigmented finishes. For purposes of performing sample testing and other activities in furtherance of maintaining color quality, it is necessary to first determine an appropriate means for "measuring" and "describing" color. A substantial amount of research has been performed during the past 50 years with respect to appropriate methods and standards for color measurement and description.

For purposes of describing color, and from a purely "physical" point of view, the production of color requires three things: a source of light; an object to be illuminated; and, a means for perceiving the color of the object. The means for perceiving the color can be the human eye and brain or, alternatively, electrical and electromechanical apparatus such as photosensitive detectors and associated auxiliary devices utilized for detecting light. In general, it is desirable to provide a means for measuring color so as to assess the manner in which an image will appear to a human observer, or the manner in which an image will perform in a photographic or other type of reproduction printing operation.

Although human perception and interpretation of color can be useful, reliance on such perception and interpretation can be highly subjective. That is, human nature may cause one person's perception of the color of a particular object to be substantially different from the perception of another. In addition, eye fatigue, age and other physiological factors can influence color perception. Further, visual human perception is often insufficient for color description. For example, certain object samples may be visually perceived under one light source as substantially "matching", and yet may actually have very different spectral characteristics and may be perceived as "non-matching" under another light source. In view of the foregoing, it is desirable to employ color measurement and description techniques which are objective in nature, and capable of differentiating among object samples having different color characteristics.

Various devices have been developed and are widely utilized to measure and quantitatively describe color characteristics of object samples. Many of these devices provide measurements related to the spectral characteristics of the samples. Described simplistically, when light is directed onto an object sample to be measured for color, the object may absorb a portion of the light energy, while correspondingly passing through or reflecting (if the object is opaque) other portions of the light. The color characteristics of the object sample will depend in part on the spectral characteristics of the object. That is, the effect of an object on light can be described by its spectral transmittance or reflectance curves (for transparent or opaque materials, respectively). These spectral characteristic curves indicate the fraction of the source light at each wavelength transmitted by or reflected from the materials. Such curves are a means for describing the effect of an object on light in a manner similar to the use of a spectral energy distribution curve for describing the characteristics of a source of light. Instruments utilized for generating such spectral characteristics curves are typically referred to as spectrophotometers.

Although the present invention is disclosed with respect to use in a spectrophotometer, it is worthwhile, for purposes of background, to describe the use of other color measurement devices. In particular, for purposes of background description of typical types of components employed in many color measurement devices, concepts associated with a reflectance densitometer are set forth in the following paragraphs.

In accordance with conventional optical physics, its is known that the proportion of light incident to an object sample and absorbed by such a sample is independent of the light intensity. Accordingly, a quantitative indication of the spectral characteristics of an object sample can be defined as the "transmittance" or "reflectance" of the sample. That is, the transmittance of a substantially transparent object can be defined as the ratio of power transmitted over light power incident to the sample. Correspondingly, for an opaque object sample, the reflectance can be defined as the ratio of power reflected from the object over the incident light power.

For collimated light, these ratios can be expressed in terms of intensities, rather than power. Furthermore, because of the nature of transmittance/reflectance and the optical characteristics of the human eye, it is sometimes advantageous to express these ratios in logarithmic form. Accordingly, one parameter widely used in color technology fields for obtaining a quantitative measurement or "figure of merit" is typically characterized as optical "density." The optical density of an object sample is typically defined as follows:

$$\text{Optical Density} = D = -\log_{10} T \text{ or } -\log_{10} R \qquad \text{(Equation 1)}$$

where T represents transmittance of a transparent object and R represents reflectance of an opaque object. In accordance with the foregoing, if an object sample absorbed 90% of the light incident upon the sample, and the object were opaque, the reflectance would ideally be 10%. The density of such a sample would then be characterized as unity. Correspondingly, if 99.9% of the light were absorbed, the reflectance would be 0.1% and the density would be 3. Similarly, the density of an "ideal" object reflecting 100% of the light incident upon the object would be 0.

To provide a relative measurement of color, it is possible to utilize the principles of optical density, without requiring measurement or knowledge of the absolute values of total incident light intensity or reflectance. That is, for example, it is possible to obtain relative color measurements among a series of object samples by utilizing a particular geometric configuration of light, object sample and reflectance or transmittance detector for each measurement, and standardizing the measurements in some desired manner.

In brief summary, optical density is a measurement of the modulation of light or other radiant flux by an object sample, such as a given area of a photographic print. Density measurements provide a means to assess the manner in which an image will appear to a human observer, or the way an image will perform in a film processing operation. Density measurements can be utilized to produce sensitometric curves to evaluate various printing and reproduction characteristics, as well as utilization to control various photographic operations, such as film processing.

For purposes of measuring optical densities, it is well-known to employ a device typically characterized as a "densitometer." These densitometers are often categorized as either "reflection" densitometers, employed for optical density measurements of opaque objects, or are otherwise characterized as "transmittance" densitometers. Transmittance densitometers are employed for determining spectral characteristics of various non-opaque materials.

FIG. 1 illustrates a simplified schematic representation of a known reflection densitometer configuration 100. A configuration of this type is described in detail in the commonly assigned U.S. Pat. No. 5,015,098 issued May 15, 1991 to Berg et al. Densitometer apparatus of the type shown in FIG. 1 are characterized as reflection densitometers, and utilized to provide color density measurements of opaque materials as previously described.

Referring specifically to FIG. 1, and to numerical references therein, the densitometer apparatus 100 includes a light source unit 102 having a source light 104. With respect to optical density measurements in various industrial fields relating to the optical characteristics of colored surfaces, various standards have been developed for densitometer light source illuminants. For example, densitometer light source standards have previously been described in terms of a tungsten lamp providing an influx from a lamp operating at a Planckian distribution of 3000° K. Other suggested standards have been developed by the American National Standards Institute ("ANSI") and the International Organization for Standardization ("ISO"). These source light densitometer standards are typically defined in terms of the spectral energy distribution of the illuminant. The source light 104 preferably conforms to an appropriate standard and can, for example, comprise a filament bulb meeting a standard conventionally known in the industry as 2856K ANSI. Power for the source light 104 and other elements of the densitometer apparatus 100 can be provided by means of conventional rechargeable batteries or, alternatively, interconnection to AC utility power.

The source light 104 projects light through a collimating lens 106 which serves to focus the electromagnetic radiation from the source light 104 into a narrow collimated beam of light rays. Various types of conventional and well-known collimating lenses can be employed. The light rays transmitted through the collimating lens 106 project through an aperture 108. The dimensions of the aperture 108 will determine the size of the irradiated area of the object sample under test.

Various standards have been defined for preferable sizes of the irradiated area. Ideally, the aperture 108 is of a size such that the irradiance is uniform over the entire irradiated area. However, in any physically realizable densitometer arrangement, such uniform irradiance cannot be achieved. Current standards suggest that the size of the irradiated area should be such that irradiance measured at any point within the area is at least 90% of the maximum value. In addition, however, aperture size is typically limited to the size of the color bar or color patch area to be measured, and is also sized so as to reduce stray light.

The light rays emerging from the aperture 108 (illustrated as rays 110 in FIG. 1) are projected onto the irradiated area surface of an object sample 112 under test. The sample 112 may be any of numerous types of colored opaque materials. For example, in the printing industry, the sample 112 may be an ink-on-paper sample comprising a portion of a color bar at the edge of a color printing sheet. Further, with respect to the illustrative embodiment of a spectrophotometer apparatus employing the principles of the invention as described in subsequent paragraphs herein, the sample 112 may be a portion of a painted surface comprising metallic or pearlescent particles.

As the light rays 110 are projected onto the object sample 112, electromagnetic radiation shown as light rays 114 will be reflected from the sample 112. Standard detection configurations have been developed, whereby reflected light is detected at a specific angle relative to the illumination light rays 110 projected normal to the plane of the object sample 112. More specifically, standards have been developed for detection of reflected light rays at an angle of 45° to the normal direction of the light rays 110. This angle of 45° has become a standard for reflectance measurements, and is considered desirable in that this configuration will tend to maximize the density range of the measurements. In addition, however, the 45° differential also represents somewhat of a relatively normal viewing configuration of a human observer (i.e. illumination at a 45° angle from the viewer's line of sight).

On the other hand, however, and as described in subsequent paragraphs herein with respect to an illustrative embodiment of a spectrophotometer apparatus employing the principles of the invention set forth herein, the angle of detection of reflected light may vary away from the standard angle of 45° relative to the normal direction of the light rays. Further, as also described in subsequent paragraphs herein, light may be detected at multiple angles relative to the impingement of light rays upon the object sample to be measured. Details associated with the concept of measurements at multiple angles will be set forth in subsequent paragraphs herein.

For purposes of providing light detection, a spectral filter apparatus 116 is provided. The filter apparatus 116 can include a series of filters 118, 120 and 122. The filters 118, 120 and 122 are employed for purposes of discriminating the cyan, magenta and yellow spectral responses, respectively. That is, each of the filters will tend to absorb light energy at frequencies outside of the bandwidth representative of the particular color hue of the filter. For example, the cyan filter 118 will tend to absorb all light rays, except for those within the spectral bandwidth corresponding to a red hue. By detecting reflected light rays only within a particular color hue bandwidth, and obtaining an optical density measurement with respect to the same, a "figure of merit" can be obtained with respect to the quality of the object sample coloring associated with that particular color hue.

It is apparent from the foregoing that the actual quantitative measurement of color density or color reflectance is dependent in substantial part on the spectral transmittance characteristics of the filters. Accordingly, various well-known standards have been developed with respect to spectral characteristics of densitometer filters. For example, one standard for densitometer filters is known as the ANSI status T color response. The spectral response characteristics of filters meeting this standard are relatively wide band (in the range of 50–60 nanometers (nms) bandwidth) for each of the cyan, magenta and yellow color hues. Other spectral response characteristic standards include, for example, what is known as G-response, which is somewhat similar to status T, but is somewhat more sensitive to respect to yellow hues. An E-response represents a European response standard.

Although the filters 118, 120 and 122 are illustrated in the embodiment shown in FIG. 1 as the cyan, magenta and yellow color shades, other color shades can clearly be employed. These particular shades are considered somewhat preferable in view of their relative permanence, and because they comprise the preferred shades for use in reflection densitometer calibration. However, it is apparent that different shades of red, blue and yellow, as well as entirely different colors, can be utilized with the densitometer apparatus 100.

The spectral filters 118, 120 and 122 may not only comprise various shades of color, but can also be one of a number of several specific types of spectral response filters. For example, the filters can comprise a series of conventional Wratten gelatin filters and infrared glass. However, various other types of filter arrangements can also be employed.

The spectral filters 118, 120 and 122 are preferably positioned at a 45° angle relative to the normal direction from the plane of the object sample 112 under test. In the particular example shown in FIG. 1, each of these filters is maintained stationary and utilized to simultaneously receive light rays reflected from the object sample 112.

As further shown in FIG. 1, the portion of the reflected light rays 114 passing through the filters 118, 120 and 122 (shown as light rays 124, 126 and 128, respectively) impinge on receptor surfaces of photovoltaic sensor cells. The sensor cells are illustrated in FIG. 1 as sensors 132, 134 and 136 associated with the spectral filters 124, 126 and 128, respectively. The sensors 132, 134 and 136 can comprise conventional photoelectric elements adapted to detect light rays emanating through the corresponding spectral filters. The sensors are further adapted to generate electrical currents having magnitudes proportional to the intensities of the sensed light rays. As illustrated in FIG. 1, electrical current generated by the cyan sensor 132 in response to the detection of light rays projecting through the filter 118 is generated on line pair 138. Correspondingly, electrical current generated by the magenta sensor 134 is applied to the line pair 140, while the electrical current generated by the yellow sensor 136 is applied as output current on line pair 142. Photoelectric elements suitable for use as sensors 136, 138 and 140 are well-known in the art, and various types of commercially-available sensors can be employed.

The magnitude of the electrical current on each of the respective line pairs will be proportional to the intensity of the reflected light rays which are transmitted through the corresponding spectral filter. These light rays will have a spectral distribution corresponding in part to the product of the spectral reflectance curve of the object sample 112, and the spectral response curve of the corresponding filter. Accordingly, for a particular color shade represented by the spectral response curve of the filter, the magnitude of the electrical current represents a quantitative measurement of the proportional reflectance of the object sample 112 within the frequency spectrum of the color shade.

As further shown in FIG. 1, the sensor current output on each of the line pairs 138, 140 and 142 can be applied as an input signal to one of three conventional amplifiers 144, 146 and 148. The amplifier 144 is responsive to the current output of cyan sensor 132 on line pair 138, while amplifier 146 is responsive to the sensor current output from magenta sensor 134 on line pair 144. Correspondingly, the amplifier 148 is responsive to the sensor current output from yellow sensor 136 on line pair 142. Each of the amplifiers 144, 146 and 148 provides a means for converting low level output current from the respective sensors on the corresponding line pairs to voltage level signals on conductors 150, 152 and 154, respectively. The voltage levels of the signals on their respective conductors are of a magnitude suitable for subsequent analog-to-digital (A/D) conversion functions. Such amplifiers are well-known in the circuit design art, and are commercially available with an appropriate volts per ampere conversion ratio, bandwidth and output voltage range. The magnitudes of the output voltages on lines 150, 152 and 154 again represent the intensities of reflected light rays transmitted through the corresponding spectral filters.

Each of the voltage signal outputs from the amplifiers can be applied as an input signal to a conventional multiplexer 156. The multiplexer 156 operates so as to time multiplex the output signals from each of the amplifiers 144, 146 and 148 onto the conductive path 158. Timing for operation of the multiplexer 156 can be provided by means of clock signals from master clock 160 on conductive path 162. During an actual density measurement of an object sample, the densitometer 100 will utilize a segment of the resultant multiplexed signal which sequentially represents a voltage output signal from each of the amplifiers 144, 146 and 148.

The resultant multiplexed signal generated on the conductive path 158 is applied as an input signal to a conventional A/D converter 164. The A/D converter 164 comprises a means for converting the analog multiplexed signal on conductor 158 to a digital signal for purposes of subsequent processing by central processing unit (CPU) 166. The A/D converter 164 is preferably controlled by means of clock pulses applied on conductor 168 from the master clock 160. The clock pulses operate as "start" pulses for performance of the A/D conversion. The A/D converter 164 can be any suitable analog-to-digital circuit well-known in the art and can, for example, comprise 16 binary information bits, thereby providing a resolution of 65K levels per input signal.

The digital output signal from the A/D converter 164 can be applied as a parallel set of binary information bits on conductive paths 170 to the CPU 166. The CPU 166 can provide several functions associated with operation of the densitometer apparatus 100. In the embodiment described herein, the CPU 166 can be utilized to perform these functions by means of digital processing and computer programs. In addition, the CPU 166 can be under control of clock pulses generated from the master clock 160 on path 172. However, a number of the functional operations of CPU 166 could also be provided by means of discrete hardware components.

In part, the CPU 166 can be utilized to process information contained in the digital signals from the conductive paths 170. Certain of this processed information can be generated as output signals on conductive path 176 and applied as input signals to a conventional display circuit 178. The display circuit 178 provides a means for visual display of information to the user, and can be in form of any one of several well-known and commercially-available display units.

In addition to the CPU 166 receiving digital information signals from the conductive paths 170, information signals can also be manually input and applied to the CPU 166 by means of a manually-accessible keyboard circuit 180. The user can supply "adjustments" to color responses by means of entering information through the keyboard 180. Signals representative of the manual input from the keyboard 180 are applied as digital information signals to the CPU 166 by means of conductive path 182.

In general, the most commonly used instruments for "measuring" color now in commercial use are spectrophotometers, colorimeters and densitometers. While the three types of instrumentation are employed to measure reflected or transmitted light, a spectrophotometer typically measures light at a number of points on the visible spectrum, thereby resulting in a curve. With reference to FIG. 1, a spectrophotometer may have a similar configuration to the densitometer 100, but instead of having only three pairs of filters and photodiodes, a spectrophotometer may have, for example, sixteen or more pairs of filter and photodiode configurations. Each of the filters would be associated with a substantially separate portion of the visible light spectrum, for purposes of obtaining a curve representative of reflectance (for opaque objects) characteristics of various object samples. Typically, with a spectrophotometer, the output variable represented by the curve (as a function of wavelength) represents a percentage reflectance value. A spectrophotometer is considered essential in the color formulation of many products. Such products can vary from solid, opaque objects (such as ceramics and metals) to transparent liquids, such as varnishes and dye solutions.

A colorimeter, in contrast to a spectrophotometer, typically is utilized to measure light in a manner similar to the human eye, i.e. with utilization of red, green and blue (or similar colors) receptors. Colorimeters are utilized for many applications, including the measurement of printed colors on products such as packages, labels and other materials, where a product's appearance may be considered substantially critical for buyer acceptability. Such colorimeters will typically provide output in the form of tristimulus values or, alternatively, in the form of other values which tend to relate more specifically to appearance attributes of colors. For example, chromaticity coordinates are often utilized.

Spectrophotometer and colorimeter apparatus are commonly used for purposes of measuring color characteristics of painted surfaces. When manufacturing painted surfaces having pigmented finishes, it can be somewhat difficult to readily obtain a color "match" with a standard for the painted surface. In this regard, a spectrophotometer or colorimeter apparatus can be utilized for purposes of providing data to assist in adjusting formula pigment compositions to provide optimal matching of pigmented finishes with color standards. The manipulation of formula pigment compositions is typically referred to as "shading."

With conventional paints or other types of pigment compositions, a "color quality" measurement with sufficient tolerances can typically be obtained through the use of a single light source illuminating the object sample to be tested from a single illuminant. Correspondingly, with such paints and other pigment compositions, it is typically sufficient to utilize a single reflectance angle or "angle of detection" for the light rays reflected from the colored surface.

However, in many industries today, more complex paints and other pigment compositions are being employed. For example, in industries such as the automotive industry, paints are being utilized which employ light-reflecting particles or "flakes."These types of paints and other pigment compositions are typically referred to as "metallic" paints. The majority of automobiles currently being manufactured employ such metallic painted surfaces. With such automotive paints, a primer is first applied to the surface of the automobile. A base coat is then applied over the primer. Such base coat comprises a colored paint having metallic particles dispersed within the paint. The metallic particles are composed of materials such as aluminum, coated mica and the like. After application of the base coat comprised of the metallic particles, a "clear" coat is then applied. The clear coat essentially blocks ultraviolet light and maintains a gloss appearance for the painted surface.

Another type of color material which is currently being employed in the automotive industry comprises what is known as "pearlescent" paint. Pearlescent color materials typically utilize a three-coat system, in addition to the primer applied to the surface. A second coat is provided between the base coat and the clear coat. In part, the second coat can also include pearlescent particles.

With metallic color materials, a "lightness" or color change is exhibited with the viewing angle. That is, such color materials change visual appearance relative to the angle of view. With pearlescent materials, an actual color change is exhibited with a change in the viewing angle. Such metallic and pearlescent materials are particularly desirable with finishes for products such as automobiles, because the change in visual appearance tends to accentuate the contours of the automobile. That is, a change in the lightness or color will tend to cause the painted product to appear to have greater curvature. Accentuation of curvature, for aesthetic purposes, tends to increase the "glamour" of the product.

With metallic and pearlescent color materials, a single color measurement reading at a given angle for a spectrophotometer or colorimeter will not provide a color "quality" measurement which is sufficiently accurate to characterize the color characteristics of the paint. For purposes of fully characterizing the color characteristics of metallic or pearlescent materials, measurements at several different angles of view must typically be obtained. A substantial amount of developmental work has been undertaken with respect to determination of appropriate measuring techniques for determining color characteristics of metallic or pearlescent materials. For example, three-dimensional plots of spectral curves as a function of viewing angle have been obtained. However, such plots of spectral curves are substantially impractical for purposes of industrial color matching and control. Instead, development has been directed toward determining what could essentially be characterized as a "least" number of measurement angles providing sufficient information with respect to goniophotometric characteristics of a color, consistent with visual response, and sufficient to draw conclusions within industrial color matching tolerances.

For purposes of providing multiple viewing angles for metallic or pearlescent color materials, various types of procedures are known in the art. For example, it is known to utilize a detection arrangement comprising a fixed viewing angle relative to the direction of illumination, with rotation of the painted sample to be analyzed. Such arrangement is commonly known in the art as "object modulation." However, as readily apparent, such object modulation is substantially difficult with any object of relatively large size. Also, tolerances associated with the apparatus for rotation of the object sample under test must be extremely small, and large and expensive equipment is required for such rotation.

When the viewing angle is essentially "moved" to different positions, relative to the direction of illumination from a light source, such an arrangement is typically characterized as "detector modulation." Correspondingly, a third arrangement is commonly referred to as "source modulation." With source modulation, the object sample under test and the viewing angle are fixed, while the direction of illumination is varied. In any event, prior studies appear to have indicated that the measured color of such metallic or pearlescent color materials is primarily a function of the angle relative to the specular angle.

From the substantial prior development which has occurred with respect to characterization of goniophotometric characteristics of metallic and pearlescent color materials, it has essentially been concluded that for purposes of practicality, such color materials can be effectively characterized by measurement at three angles. This determination has been made in part through experimentation, as well as through various calculations. For example, within the prior art, the light reflected from a metallic finish has been characterized as being capable of analysis on the basis that such light has a diffused component (for multiple reflections with flake and other pigments) and a flake component (from a single reflection from a flake). The flake component, in addition to having an overall magnitude, can be characterized as having an angular distribution dominated by a single statistical characteristic of the flake orientation. With this single statistical characteristic, only two measurements are required for quantification of the same. When the metallic or pearlescent color materials are viewed from a direction substantially away from the specular angle, the color characteristic measurement is dominated by the diffused component. Correspondingly, the flake component dominates when viewing from a direction relatively close to the specular angle. Accordingly, it is argued that one angle of measurement should be substantially away from the specular angle, while another angle should be as close to specular as possible, while excluding "first surface" reflection. The third angle should be intermediate the other two angles at a location where the flake component is both significant and significantly different from that in the other measurements.

Other studies have involved the goniocolorimeteric characteristics of a substantial number of metallic colors covering several flake types and color pigmentations. Measurements were obtained of these metallic colors with respect to lightness, hue and chroma as a function of normalized angle. In these studies, the lightness response exhibited a relatively complex structure, and was thus chosen for polynomial modeling. Residual errors observed for each model were a measure of the information not obtainable from the "fit" of the model. It was found that linear models were relatively inadequate in modeling the curvature of the response, thereby leaving a relatively large residual error. Quadratic models having three appropriate chosen measurement angles were characterized as dramatically reducing the average residual sum of squares. Correspondingly, the use of four angles gave a relatively slight further reduction in a residual sum, although not sufficient so as to justify the increased complexity which is required in data handling from four measurement angles.

In summary, several previous studies have indicated that measurement of the optical properties of metallic or pearlescent color materials at only two specified angles can provide some useful characteristics. Such arrangements are discussed in Armstrong, Jr. et al, U.S. Pat. No. 3,690,771 issued Sep. 12, 1972. However, it has generally been accepted in the industry today that three angles of measurement are substantially optimal for purposes of determining color characteristics of metallic and pearlescent color materials. For example, Alman, U.S. Pat. No. 4,479,718 issued Oct. 30, 1984, is directed to an instrument for determining color characteristics of paints having reflecting flakes. The Alman patent describes an arrangement whereby the paint sample is illuminated by a single light source, with the light reflected by the paint sample being detected by a series of three detectors positioned at various angles. By utilizing the combined reflectance measurements of the three detectors, a "compensation" for the differing metallic reflecting qualities is achieved.

Alman further describes the concept that reflectance factors can be utilized to calculate color descriptor values for purpose of specifying color and color difference. Tristimulus values of a color can be calculated by combining the reflectance factor data with data on the sensitivity of the human eye and the irradiance of a light source, all as functions of wave length in the visible spectrum. The tristimulus values can be utilized to calculate color descriptors which relate to visual perception of color and color difference. For example, one set of descriptors which can be utilized are the CIE L*a*b* perceptual color scales as recommended by the International Commission on Illumination.

Transformations of the tristimulus values can be used to calculate various perceptual color values in accordance with equations set forth in the Alman patent. Alman further describes various theory associated with the determination of mathematical models for purposes of determining an optimal number of angles for purposes of measurement. Alman concludes that three properly selected measurement angles provide an optimized selection for purposes of determining maximum information on metallic color for relatively minimum measurement effort. Alman also describes the concept of providing an incident light source positioned at angle of 45° relative to a surface comprising a paint film. Three detectors are position at three different angles, namely 15°, 45°, and 110° as measured from the specular angle. Although Alman describes the concept of employing a single light source with multiple detectors, apparatus associated with operation of the detectors is not specifically described within the application.

In another arrangement, Steenhoek, U.S. Pat. No. 4,917,495 issued Apr. 17, 1990, describes a colorimeter and method for characterizing optical properties of a colored surface comprising metallic or pearlescent particles. The Steenhoek arrangement utilizes three multiangular spectrophotometric measurements to derive color constants for the surface.

The Steenhoek colorimeter specifically utilizes three sources of illumination comprising three separate lamps. The output of the lamps is collimated by achromatic source lenses mounted at the corresponding focal lengths from the lamp filament. Collection optics are included which comprise achromatic collection lenses mounted at twice their corresponding focal lengths from a sample surface. A monochrometer, comprising a diffraction grating and a silicone diode array detector, is mounted opposite to the sample side of the lens. An entrance slit to the monochrometer is mounted at a distance of one focal length from the lens. Such an arrangement permits only light which is very nearly collimated to pass through the entrance slit, permitting only light scatter at or about 45° from the sample normal to enter the monochrometer.

After passing through the entrance slit, light diverges until it impinges upon the diffraction grating. At the diffraction grating, the light is dispersed and refocused onto a silicone diode array detector having 12 detecting elements. Each of the detecting elements includes an associated amplifier which converts diode current to a voltage signal. The 12 signals are then multiplexed and digitized by an analog to digital converter. All of the functions of the colorimeter are controlled by a microcomputer, and measurement data derived from the instrument is displayed on an LCD display. Within the colorimeter, the sample to be measured is sequentially illuminated from minus 30°, 0° and 65° as measured from a sample normal. Light reflected from the sample is detected at 45° as measured from the sample normal.

In accordance with the foregoing, concepts associated with multi-angular measurements of color materials employing metallic or pearlescent particles are relatively well known. However, these known systems typically require a substantial number of optical elements. For example, although not specifically described in the Alman patent, it appears that each of the detector arrangements shown therein would require separate detection circuitry for providing electrical signals representative of the detected light rays. Correspondingly, with respect to the Steenhoek patent, three illumination sources are required. Still further, although Steenhoek is described as a portable device, it is not clear that the device described in the Steenhoek patent would include a power source, except for a source separate from the primary unit.

SUMMARY OF THE INVENTION

In accordance with the invention, an apparatus is provided which is adapted for measuring color characteristics of a colored surface. The apparatus includes light source means for projecting light toward the colored surface at at least one angle of illumination relative to the surface. Light receiving means are provided for receiving light rays reflected from the colored surface at a plurality of reflection angles relative to the surface.

Detection means are also provided, which are connected to the light receiving means. The detection means provides a means for detecting the light rays reflected from the colored surface, and for generating electrical signals representative of spectral characteristics of the surface, for each of a series of spectral segments across the visible light spectrum. Processing means are connected to the detection means and responsive to the electrical signals for generating data representative of the spectral characteristics. The apparatus also includes switching means positioned adjacent to the light receiving means for periodically inhibiting the light rays reflected from the colored surface from being received by a subset of the light receiving means.

In accordance with another aspect of the invention, the detection means comprises only a single array of filtered photodetectors. Each of the filtered photodetectors include a filter and a photodetector. Each filter associated with a corresponding photodetector comprises a spectral response characteristic different from filters associated with all other photodetectors of the array. In addition, the light receiving means comprises a plurality of optical fiber bundles. At any given time, the switching means inhibits light rays reflected from the colored surface from being received by all but one of the optical fiber bundles. The light rays reflected from the colored surface and received through all of the optical fiber bundles are applied to the array of filter photodetectors.

In accordance with another aspect of the invention, the light source means projects light toward the colored surface only at one angle of illumination relative to the surface. The light receiving means receives the light rays reflected from the colored surface at three reflection angles relative to the surface. In accordance with one particular aspect of the invention, the three reflection angles are substantially equal to 25°, 45°, and 110° relative to a specular angle.

In accordance with a further aspect of the invention, the switching means includes shutter means positioned adjacent the light receiving means for periodically and mechanically inhibiting the light rays reflected from the colored surface from being received by a subset of the light receiving means. The shutter means is movable among open and closed positions. Motive means coupled to the shutter means and responsive to the processing means can move the shutter means among the open and closed positions. The shutter means includes a pair of optical shutter devices. Each of the shutter devices includes a pair of optical shutters positioned substantially at a 90° angle relative to each other. A rotatable portion is connected to the pair of optical shutters, and an arm follower is connected to the rotatable portion and coupled to the motive means. The motive means includes a pair of motors, with each of the motors being operably coupled to a different one of the optical shutter devices.

A first one of a first pair of the pairs of optical shutters is responsive to the motive means to periodically inhibit the light rays reflected from the colored surface from being received by a first one of the plurality of optical fiber bundles. A second one of the first pair of the pairs of optical shutters is responsive to the motive means to periodically inhibit the light rays reflected from the colored surface from being received by a second one of the plurality of optical fiber bundles. Correspondingly, a first one of a second pair of the pairs of optical shutters is responsive to the motive means to periodically inhibit the lights rays reflected from the colored surface from being received by the second one of the plurality of optical fiber bundles. A second one of the second pair of the pairs of optical shutters is responsive to the motive means to periodically inhibit the light rays reflected from the colored surface from being received by a third one of the plurality of optical fiber bundles.

In accordance with another aspect of the invention, the apparatus is enclosed in a hand-held and portable structure. In addition, the apparatus includes means for testing for light leak by detecting light rays reflected from a colored surface in the absence of illumination by the light source means, and while the subset of the light receiving means is inhibited from receiving the light rays.

In accordance with another aspect of the invention, a method is provided for measuring color characteristics of a colored surface. The method includes the steps of projecting light toward the colored surface at a single angle of illumination relative to the surface, and receiving light rays reflected from the colored surface through a plurality of optical fiber bundles at a plurality of reflection angles relative to the surface. The light rays reflected from the colored surface are detected and electrical signals are generated representative of spectral characteristics of the surface, for each of a series of spectral segments across the visible light spectrum. Data is generated representative of the spectral characteristics in response to the electrical signals. In addition, the method includes periodically inhibiting the light rays reflected from the colored surface from being received by a subset of the plurality of optical fiber bundles.

The method also includes maintaining the light source in an off state, and maintaining all but a first one of the optical fiber bundles in a closed position. The optical fiber bundles in a closed position are inhibited from receiving any light rays reflected from the colored surface. The first one of the optical fiber bundles is maintained in an open position, and the intensity of light rays reflected from the colored surface and received through the first one of the optical fiber bundles is measured. A determination is then made whether the measured intensity exceeds a predetermined threshold. The method also includes maintaining all but a second one of the optical fiber bundles in a closed position, and maintaining the second one of the optical fiber bundles in an open position. Intensity of light rays reflected from the colored surface and received through the second one of the optical fiber bundles is measured. A determination is then made as to equivalence or nonequivalence of the measured intensities of light rays received through the first one and the second one of the optical fiber bundles.

BRIEF DESCRIPTION OF THE DRAWINGS

The invention will now be described with respect to the drawings, in which.

DESCRIPTION OF THE PREFERRED EMBODIMENT

Figure 2:
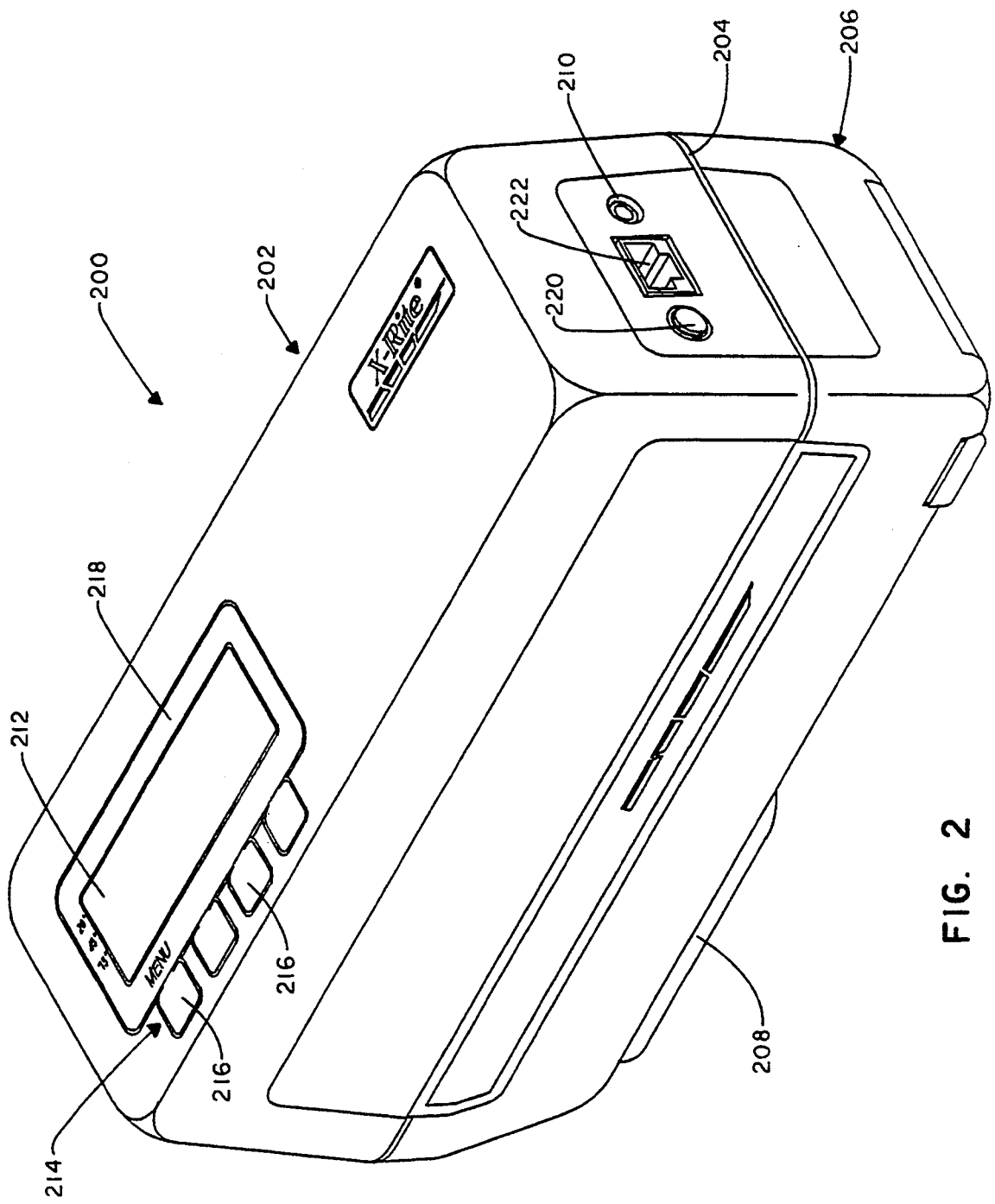
FIG. 2 is a perspective view of the entirety of the mechanical structure of a multi-angular spectrophotometer apparatus in accordance with the invention.
Figure 3:
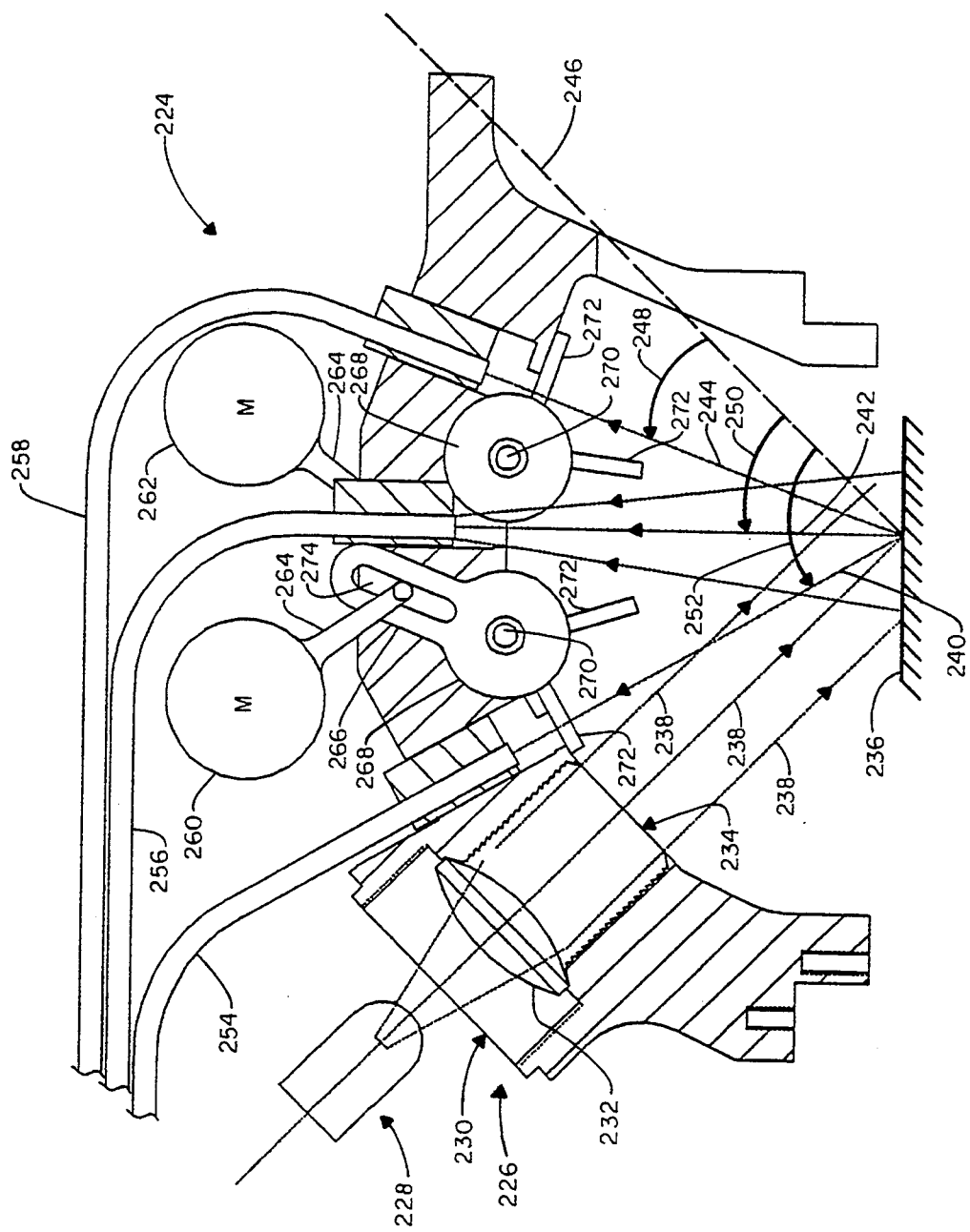
FIG. 3 is a sectional view showing a portion of the optical-mechanical structure of the spectrophotometer apparatus shown in FIG. 2, and particularly showing the optical switching configuration for the reflected light receiving structure.

The principles of the invention relate to apparatus and methods associated with multi-angular measurements of optical characteristics and are disclosed, by way of example, in a spectrophotometer apparatus 200 as illustrated in FIGS. 2 and 3. Spectrophotometer apparatus of the type shown in FIGS. 2 and 3 are characterized as reflection spectrophotometers and utilized to provide spectral response characteristics of colored materials. General concepts associated with such measurements were previously described in the section entitled "Background of the Invention."

As described in greater detail herein, the spectral response characteristics are obtained by projecting light from a single light source toward the object sample, and then measuring at multiple angles the proportion of light reflected from the object sample within each of a series of spectral segments across the visible light spectrum. In accordance with the invention, the spectrophotometer apparatus 200 provides a means for obtaining optical characteristics of color materials such as metallic or pearlescent paints, with relatively high accuracy and repeatability, and yet while still providing a hand-held and portable apparatus.

An exemplary physical structure of the spectrophotometer apparatus 200 is illustrated in relative simplistic form in FIGS. 2 and 3. Referring specifically to FIG. 2, the spectrophotometer apparatus 200 comprises a compact structure suitable for use while being hand-held, and providing complete portability. The spectrophotometer apparatus 200 includes an upper cover 202 which may have a trim strip 204 positioned therearound. Located below the upper cover 202 is a housing subassembly 206 adapted to house various components of the spectrophotometer apparatus 200.

The components of the spectrophotometer apparatus 200 include an optics assembly housed within a section of the apparatus 200 and partially shown in FIG. 2 as assembly 208. The apparatus 200 also includes a lower surface (not shown) adapted to be positioned adjacent the object sample to be tested, with the optics assembly 208 positioned substantially flush with the particular portion of the paint surface or other object sample to be tested.

As described in subsequent paragraphs herein, the spectrophotometer apparatus 200 can include a relatively conventional battery, for purposes of providing DC battery power to the apparatus 200. However, an AC adaptor input 210 is also provided for purposes of allowing use of the spectrophotometer apparatus 200 with conventional external AC power.

As further shown in FIG. 2, a visual display device 212 is also provided, which can comprise a conventional LCD display device. In addition, a keyboard 214 can be provided, having a series of key switches 216. The key switches 216 associated with the keyboard 214 can be conventional switches for providing manual input entry for the spectrophotometer apparatus 200. A display cover 218 can be utilized to aesthetically cover the visual display device 212 in the manner shown primarily in FIG. 2.

With further reference to FIG. 2, an enable switch 220 is also provided, for purposes of enabling and disabling the spectrophotometer apparatus 200. In addition, as described in subsequent paragraphs herein, the spectrophotometer apparatus 200 can be adapted to transmit or receive data from external computers or other devices. For this purpose, an external port 222 is also provided. Preferably, the external port 222 can employ a conventional RS232 interface configuration. Concepts associated with the use of a color measurement device and an interface for communication with external devices are disclosed in the commonly assigned Peterson et al U.S. Pat. No. 4,591,978 issued May 27, 1986.

In accordance with the invention, the spectrophotometer apparatus 200 provides for the use of multi-angular measurements of an object sample under test, such as an automobile panel surface having a metallic or pearlescent paint film. However, further in accordance with the invention, the multi-angular measurements are obtained with the use of only a single light source and a plurality of light receiving devices which apply light reflected from the object sample to a single array of photodetectors. As described in subsequent paragraphs herein, only a single array of photodetectors is required in view of sequential switching of the enabling of the light receiving devices through the use of an electromechanical "shuttering" arrangement.

The foregoing concepts are illustrated in the depiction of an exemplary optical/mechanical structure as shown in FIG. 3. The structure, identified as optical/mechanical structure 224, includes a light source unit 226 having a lamp 228 which projects light through an aperture 230 and through a collimating lens 232. Various standards have been developed for a spectrophotometer for light source illuminants such as lamp 228, for spectral reflectance measurements in various industrial and commercial fields. For example, standards have previously been described in terms of a tungsten lamp providing an influx from a lamp operating at a Planckian distribution of 3000K. Other suggested standards have been developed by ANSI and the International Organization for Standardization ("IOS"). In addition, various CIE illuminants have also been defined, for calculations under various lighting conditions. Such light source standards are typically defined in terms of the spectral energy distribution of the illuminant. The lamp 228 preferably conforms to an appropriate standard and can, for example, comprise a filament meeting a standard conventionally known in the industry as 2856K ANSI. The light source 226 comprising the lamp 228 can be operated or under control of a conventional lamp control circuit as described in subsequent paragraphs herein, and power to the lamp control circuit can be provided through a battery supply associated with the apparatus 200.

The lamp 228 projects light through the aperture 230 and through the collimating lens 232. The collimating lens 232 serves to focus electromagnetic radiation from the lamp 228 into a relatively narrow collimated beam of light rays. Various types of conventional and well-known collimating lenses can be employed. Light rays from the collimating lens project through a further aperture 234, with the dimensions of the aperture 234 determining the size of the irradiated area of an object sample 236. Various standards have also been defined for preferable sizes of the irradiated area. Ideally, the aperture is of a size such that the irradiance is uniform over the entire irradiated area. However, in any physically realizable spectrophotometer arrangement, such uniform irradiance cannot be achieved. Current standards suggest that the size of an irradiated area should be such that irradiance measured at any point within the area is at least 90 percent of the maximum value. In addition, however, aperture size is typically limited to the size of the particular areas to be measured, and is also sized so as to reduce stray light.

The light rays emerging from the aperture 234 are illustrated in FIG. 3 as light rays 238 and are projected onto the irradiated area surface of the object sample 236 under test. As the light rays 238 are projected onto the object sample 236 under test, electromagnetic radiation shown as light rays 240, 242, and 244 will be reflected from the object sample 236. As previously described in the section entitled "Background Of The Invention," it is necessary to obtain quantitative measurements of this reflected light for purposes of determining the relative proportions of the light reflected from various segments of the spectrum and from various object samples. As also previously described, it is substantially impossible to measure all of the light reflected from the object sample 236. Accordingly, reflected light is detected and received only at specific angles relative to the angle of illumination. For purposes of description, and in accordance with industry standards, the angles of detection are typically measured from a spectral angle which is illustrated in FIG. 3 by angle line 246. For purposes of illustration and description, FIG. 3 illustrates the angle of the reflected light wave 244 as corresponding to angle 248. Correspondingly, the light wave 242 is shown as being reflected at angle 250. Still further, reflected light wave 240 is shown as being reflected at angle 252.

In accordance with the invention, the reflected light waves 240, 242, and 244 are received by light receiving devices comprising a series of optical fiber bundles 254, 256 and 258. More specifically, optical fiber bundle 254 is positioned at angle 252 relative to the specular angle shown by line 246, and receives the reflected light waves 240. Optical fiber bundle 256 is positioned at angle 250 relative to the specular angle and receives reflected light waves 242. Still further, optical fiber bundle 258 is positioned at spectral angle 248 and receives reflected light waves 244.

In accordance with the invention, the reflected light waves 240, 242 and 244 received by the optical fiber bundles 254, 256 and 258, respectively, are applied by the fiber bundles to a single array of photodetector devices as described in subsequent paragraphs here. Further in accordance with the invention, at any given time, reflected light waves are prohibited from being received by two of the three optical fiber bundles, through the use of an electro-mechanical "shuttering" arrangement. More specifically, a shuttering arrangement in accordance with the invention comprises two motors, identified as motors 260 and 262 in FIG. 3. Each of the motors can be conventional in design and of sufficient size and power so as to be operable through the use of conventional batteries employed with the spectrophotometer apparatus 200. Each of the motors 260, 262 includes an actuator arm 264 which is capable of at least partial rotation. Each of the actuator arms 264 is slidably coupled to an arm follower 266 integral with or otherwise connected to an optical shutter device 268. Each of the optical shutter devices, 268 includes a cylindrical portion rotatably coupled to the body of the apparatus 200 or other appropriate part through an axle 270. As further shown in FIG. 3, each of the optical shutter devices 268 includes a pair of optical shutters 272 positioned substantially at 90° angles relative to each other. As further shown in FIG. 3, with the optical shutter device 268 coupled to the motor 260 in the position shown in FIG. 3, one of the optical shutters 272 is in a position so as to prohibit reflected light waves 240 from being received by the optical fiber bundle 254. Correspondingly, with the optical shutter device 268 coupled to the motor 262 and positioned as shown in FIG. 3, one of the optical shutters 272 substantially prohibits the reflected light waves 244 from being received by the optical fiber bundle 258. Further in accordance with the positional configuration of the optical shutter devices 268 as shown in FIG. 3, only the reflected light waves 242 are received by the optical fiber bundle configurations, and the light waves 242 are received only by the optical fiber bundle 256.

For purposes of allowing the optical fiber bundle 254 to receive the reflected light waves 240, the motor 260 can be actuated so as to rotate the actuator arm 264 in a clockwise direction as illustrated in FIG. 3. As further shown in FIG. 3, the actuator arm 264 is coupled to the arm follower 266 through the channel 274. With this configuration, the arm follower 266 associated with the optical shutter device 268 coupled to the motor 260 will rotate in a counter-clockwise direction as shown in FIG. 3. With this rotation, the optical shutters 272 will correspondingly rotate so that the reflected light waves 240 can be received through the optical fiber bundle 254, while one of the optical shutters 272 will be positioned in part so as to prohibit the reflected light waves 242 from the being received by the optical fiber bundle 256. With this configuration, only the optical fiber bundle 254 will be receptive to any light waves reflected from the object sample 236 under test.

As apparent from the foregoing description, the motor 262 can be enabled so as to rotate the actuator arm 264 associated therewith in a counter-clockwise direction. Although not specifically shown in FIG. 3, the actuator arm 264 associated with the motor 262 is connected to the optical shutter device 268 which is not associated with the motor 260. With rotation of the actuator arm 264 of motor 262 in a counter-clockwise direction, one of the shutters 272 associated with the optical shutter device 268 will be rotated so as to prohibit reflected light waves 242 from being received by the optical fiber bundle 256. However, with the positional rotation, the optical fiber bundle 258 will be enabled so as to receive the reflected light waves 244 therethrough.

In summary, the motors 260, 262 can be operated in a manner such that each of the optical fiber bundles 254, 256 and 258 is sequentially enabled so as to receive the corresponding reflected light waves 240, 242 and 244, respectively. As will be described in part in subsequent paragraphs herein, the motors 260, 262 can be operated under control of a processor associated with the electro-mechanical circuitry of the spectrophotometer apparatus 200. With this configuration and operation of the motors 260, 262, reflected light waves are sequentially received through each of the fiber bundles 254, 256 and 258, with light waves being received through each optical fiber bundle only at a time such that no light waves are received through either of the other two optical fiber bundles. Although FIG. 3 illustrates a particular electro-mechanical shuttering or switching arrangement for sequential reception of reflected light waves through the optical fiber bundles, various other switching arrangements can be employed for providing such optical switching, without departing from the novel concepts of the invention. Still further, the invention is not limited to any particular ones of the angles 248, 250 or 252 corresponding to the angles of reflection relative to the specular angle. As an illustrative embodiment, angle 248 can be 25°, angle 250 can be 45°, and angle 252 can be 110°.

Figure 1:
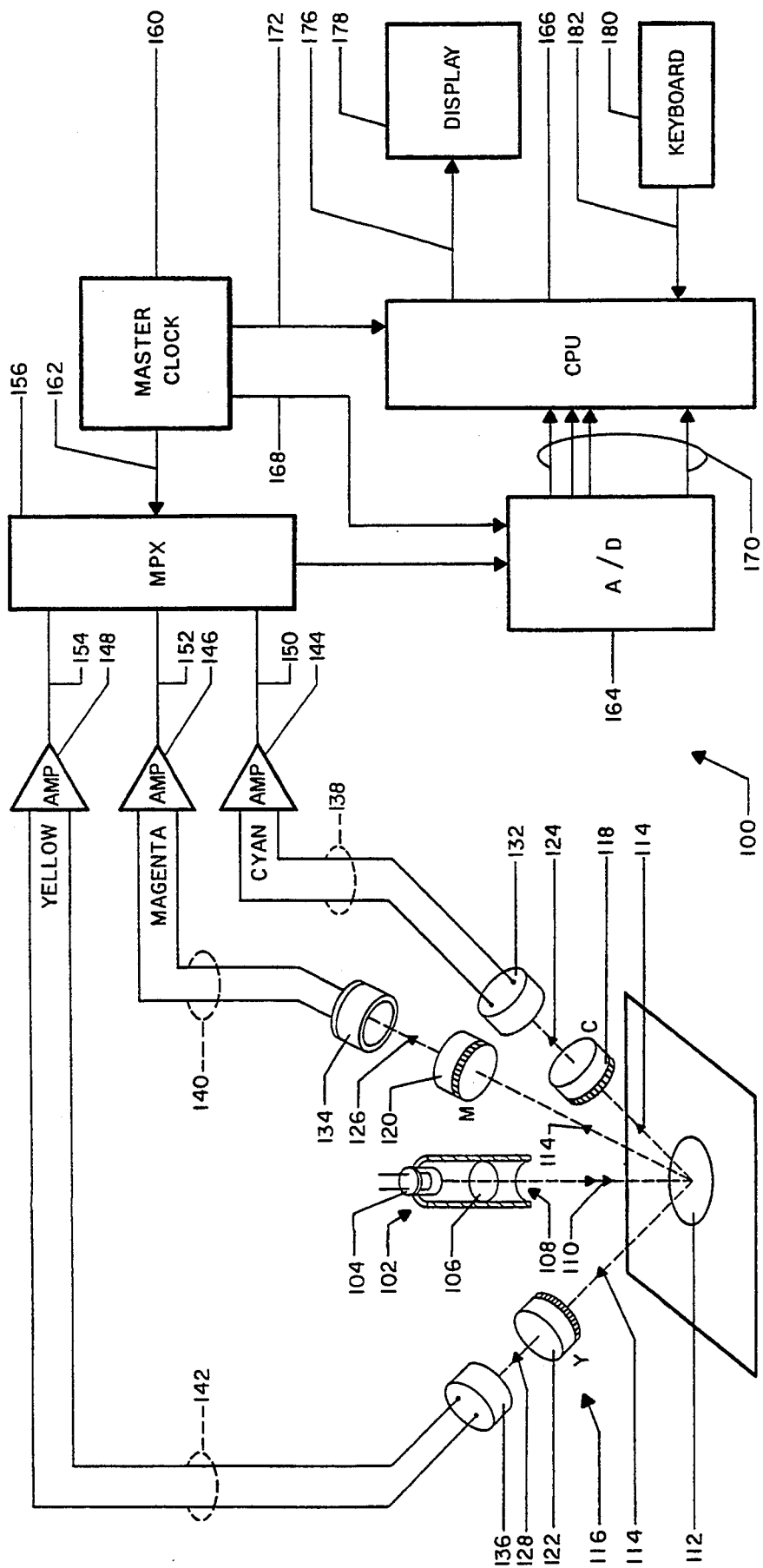
FIG. 1 is an illustrative embodiment of a prior art color measuring device comprising a densitometer.
Figure 4:
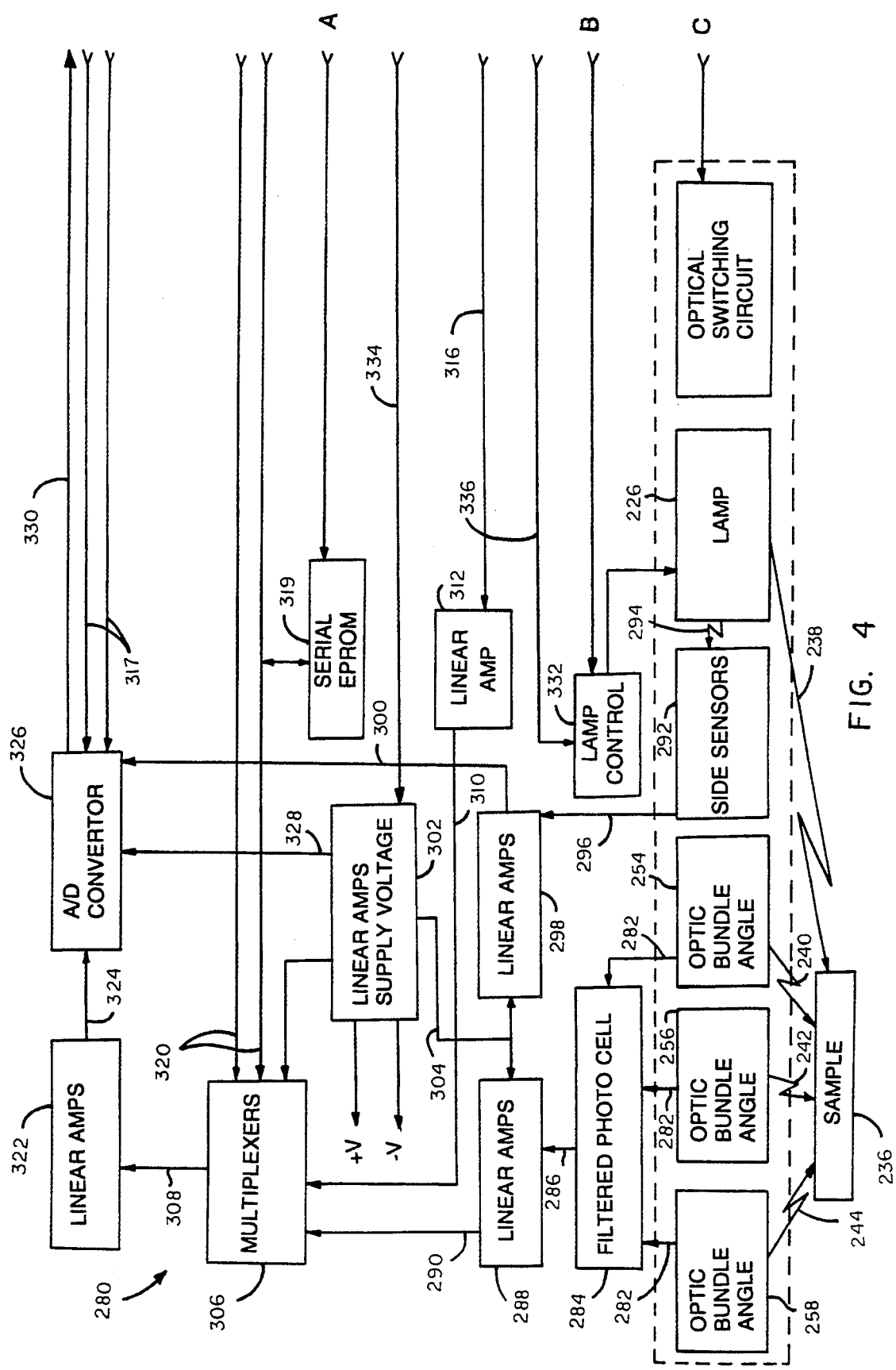
FIG. 4 is a block diagram showing the electro-optical structure of the spectrophotometer apparatus shown in FIG. 3.
Figure 4A:
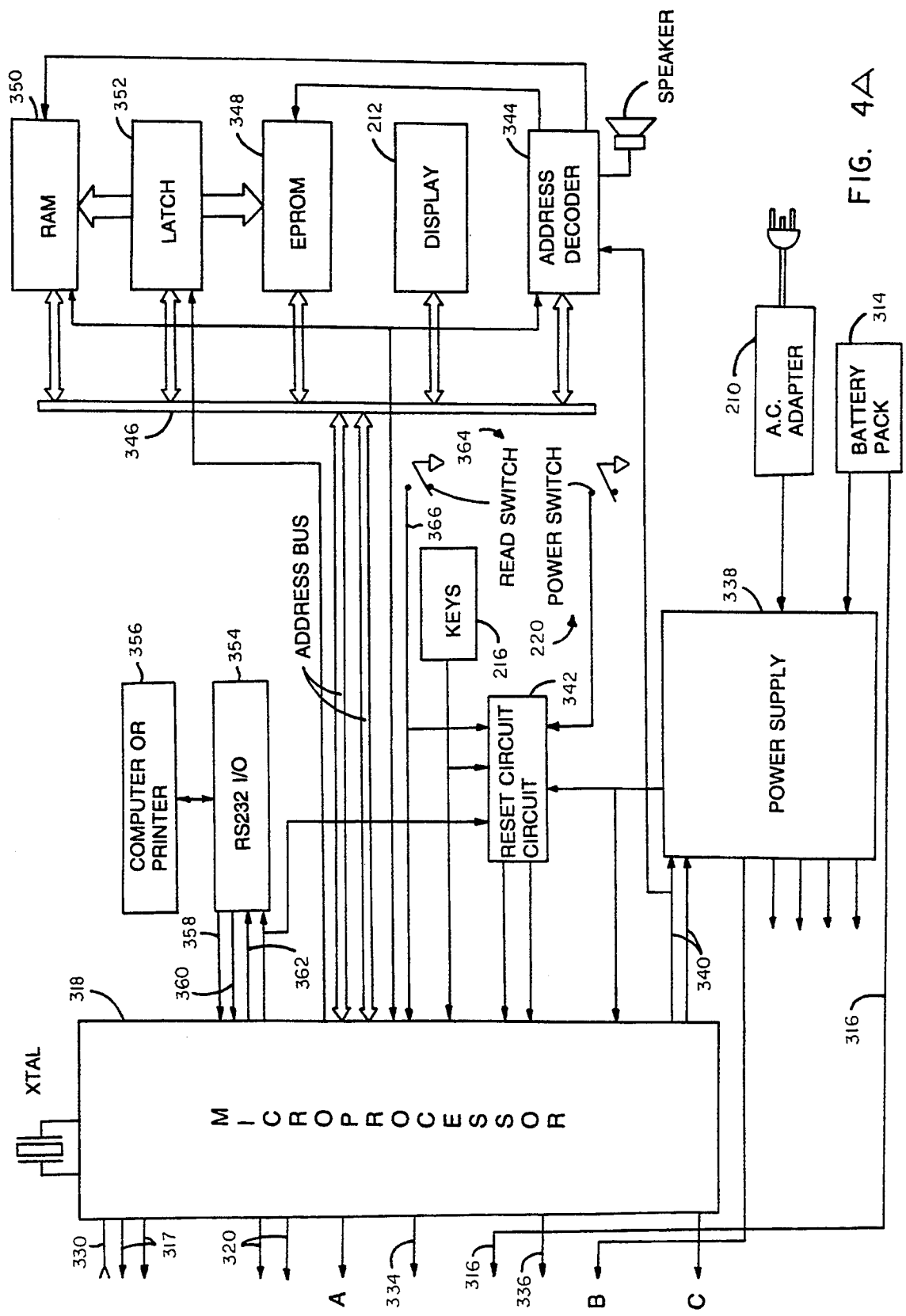

A circuit configuration 280, comprising an exemplary embodiment of the circuitry of spectrophotometer apparatus 200 which can be utilized in accordance with the invention, is primarily illustrated in FIG. 4. A number of the components of the circuit configuration 280 are similar in structure and function to components of the densitometer apparatus 100 previously described with respect to FIG. 1 in the section entitled "Background of the Invention." The principal components of the circuit configuration 280 as shown in FIG. 4 are relatively well known in the art.

As previously described, apparatus 200 comprises a spectrophotometer apparatus for purposes of providing output data in the form of spectral characteristics of an object sample 236 under test. As shown in FIG. 4, the spectrophotometer apparatus 200 and the circuit configuration 280 include a light source unit 226 utilized for measuring the spectral response characteristics of the object sample 236. With reference to FIG. 2, for purposes of measuring the object sample 236 under test, the sample 236 would be positioned underneath the optics assembly 208. In the particular configuration illustrated in FIG. 4, the spectrophotometer apparatus 200 is adapted to measure spectral reflection characteristics. However, it should be emphasized that certain aspects of the invention could be employed in color measurement apparatus varying in function from the spectrophotometer apparatus 200.

As previously described with respect to FIG. 3, various standards have been developed for spectrophotometer light source illuminants for spectral reflectance measurements in various industrial and commercial fields. As also described with respect to FIG. 3, the light source unit 226 can include a lamp 228 and collimating lens 232, with the light source unit 226 transmitting light rays 238 to the surface of the object sample 236 under test. As the applied light rays 238 project onto the object sample 236, electromagnetic radiation shown as light rays 240, 242 and 244 will be reflected from the object sample 236. These light rays and the angles of reflection associated therewith were previously described with respect to FIG. 3. As also previously described with respect to FIG. 3, the reflected light rays 240, 242 and 244 are received by optical fiber bundles 254, 256 and 258, respectively. The optical fiber bundles 254, 256 and 258 receive the corresponding reflected light rays at angles 252, 250 and 248, respectively. The reflected light rays 240, 242, and 244 are sequentially in time received by the optical fiber bundles 254, 256 and 258, respectively, with only one of the optical fiber bundles being enabled at any given time to receive the reflected light rays. An exemplary means for providing the sequential reception of the reflected light rays by the optical fiber bundles comprises the electromechanical shuttering arrangement depicted and previously described with respect to FIG. 3.

With further reference to FIG. 4, the light received by the optical fiber bundles 254, 256 and 258 is applied on symbolic paths 282 to a single array of filtered photocells 284. The photocell array 284 comprises relatively conventional circuitry with a predetermined number of "segmented" filter/photocell detection circuits, with each circuit corresponding to a different portion of the visible light spectrum in accordance with the spectral characteristics of the particular filter associated with the corresponding photocell. That is, a separate filter and photocell will be provided for each segment.

It should be emphasized that the light rays applied to the filtered photocells 284 from each of the optical fiber bundles will be applied in their entirety to the entire array of filtered photocells 284. Also, in accordance with the previously described switching arrangement, at any given time, light rays from only one of the symbolic paths 282 will be applied to the filtered photocells 284. At any given time, although the circuitry associated with the spectrophotometer apparatus 200 need not include specific circuitry for inhibiting application of light rays from two of the three symbolic paths 282, two of the three symbolic paths 282 at any given time will have no light rays associated therewith in view of the prohibiting of reception of light from the two corresponding optical fiber bundles at such time.

As is well known in the design of spectrophotometers, each of the filters associated with the filtered photocells 284 will have a different spectral frequency response, so that the entire array of filters will provide an indication of spectral characteristics of the reflected light across the entirety of the visible light spectrum. For example, each of the filters (corresponding to an associated spectral "segment")can have a bandwidth substantially in the range of 20 nanometers (nms), with each of the filters having a center frequency spaced apart approximately 20 nms from filters having adjacent frequency responses. That is, each of the filters will tend to absorb light energy at frequencies outside of the bandwidth representative of the particular spectrum portion of the filter. In this manner, with each of the filters representative of a different "segment" and different portion of the visible light spectrum, a quantitative measurement of the light reflected from the object sample and passing through each filter will provide an indication of the proportion of light reflected from the object sample within the particular frequency bandwidth of the filter. Accordingly, for a given predetermined number of filters or segments, a corresponding number of "points" can be obtained for the spectral response characteristic curve for the object sample. For example, a series of 16 segments comprising 16 pairs of filters/photocells can be employed, with each of the filters having a bandwidth of approximately 20 nms. However, various other numbers of filters and various bandwidth ranges can also be employed without departing from any of the novel concepts of the invention.

It is apparent from the foregoing that the actual quantitative measurement of reflectance for a particular segment is dependent in substantial part on the spectral transmittance characteristics of the filters. Accordingly, various well-known standards have been developed with respect to spectral characteristics of color measurement device filters. For example, with respect to densitometer apparatus, standards were previously described for the prior art densitometer apparatus 100 illustrated in FIG. 1. Again, a various number of filters and segments, with corresponding varying bandwidths, can be employed with respect to spectrophotometer apparatus 200 in accordance with the invention. However, in accordance with the invention, a particular advantage is obtained through the use of only a single array of filtered photocells 284, notwithstanding the use of multiple optical fiber bundles 254, 256 and 258. In particular, to achieve portability and to avoid a requirement of compensation among multiple filtered photocell arrays, the single array of filtered photocells 284 provides a significant advantage.

Continuing to refer to the filtered photocells 284, the configuration 284 can comprise a series of cells such as photovoltaic sensor cells (not specifically shown outside of the configuration 284). A sensor cell would be positioned essentially behind each of the filters, so that the light rays passing through the filters would impinge on receptor surfaces of the sensor cells. Accordingly, the configuration 284 would comprise a separate sensor cell associated with each of the separate filters. Such sensor cells can comprise conventional photoelectric elements adapted to detect the light rays emanating through the corresponding spectral filters. The sensors are well known in the art of color measuring device design, and are preferably adapted to generate electrical currents having magnitudes proportional to the intensities of the sensed light rays. Various types of commercially available sensors can be employed with the filtered photocell configuration 284.

The magnitude of the electrical current comprising an output signal for each of the photocells associated with the filtered photocell array 284 will be proportional to the intensity of the reflected light rays transmitted through the corresponding spectral filter. These light rays will have a spectral distribution corresponding in part to the product of the spectral reflectance curve of the object sample 236 under test, and the spectral response curve of the corresponding filter. Accordingly, for a particular segment of the visible light spectrum represented by the spectral response curve of the filter, the magnitude of the electrical current represents a quantitative measurement of the proportion of reflectance of the object sample 236 within the frequency spectrum for which the filter readily passes visible light.

Continuing to refer to FIG. 4, the electrical currents representative of the proportion of light passing through the filters of the filtered photocell configuration 284 are applied on circuit lines of line group 286. For purposes of simplification and understanding, the line group 286 is illustrated in FIG. 4 as comprising a single directional line. However, in the physically realized circuit configuration 280, the line group 286 would comprise a separate line pair for each of the frequency segments and, correspondingly, for each of the filters and photocells of the configuration 284. That is, a line pair would be interconnected to each of the photocells of the configuration 284.

As further shown in FIG. 4, each of the electrical current signals appearing on pairs of the line group 286 are applied to a series of linear amplifiers 288. Again, for purposes of simplification and understanding, the linear amplifiers 288 are illustrated in FIG. 4 as comprising a single symbolic element. However, the linear amplifiers 288 would preferably comprise a separate linear amplifier for each of the segments of the spectrophotometer apparatus 200, with each line pair of the line group 286 interconnected to a separate one of the linear amplifiers 288. The linear amplifiers 288 can be conventional in structure and function, and responsive to the electrical current output signals of the associated photocell sensors to provide a means for converting low level output current from the respective sensor and the corresponding input line pair to a voltage level signal generated as an output signal for each linear amplifier. The voltage level of the output signal of each linear amplifier is preferably of a magnitude suitable for subsequent analog-to-digital (A/D) conversion functions. Such amplifiers are well known in the circuit design art and are commercially available with an appropriate volts per ampere conversion ratio, bandwidth and output voltage range. The voltage output signal from each of the linear amplifiers 288 is applied as an output signal to separate ones of the line group 290.

The spectrophotometer apparatus 200 can also include side sensors 292 utilized to compensate for changes in lamp intensity of the light source unit 226. The side sensors 292 can comprise appropriate photovoltaic sensor cells or similar sensors responsive to the light rays 294 emanating from the light source unit 226. In known arrangements employing side sensors for lamp compensation, the spectral response characteristics of the side sensors are "matched" to the spectral response characteristics of the particular detection channel or segment then being compensated. For example, in various densitometer arrangements, wherein cyan, magenta and yellow color channels may be employed, it is known to provide for matching the spectral response characteristic of the side sensor to the particular channel then being compensated. Such a matching arrangement may be achieved through the use of multiple side sensors each having a filter with a spectral response characteristic matching that of one of the channels of the densitometer or, alternatively, a single side sensor may be employed with a series of filters which are individually and sequentially "moved" into appropriate positions so as to provide a response characteristic matching that of the then currently evaluated color channel. Similar arrangements have been employed in other color measuring devices, such as spectrophotometers.

Other arrangements are known wherein the employment of side sensors in a spectrophotometer apparatus do not include any "changing" of spectral response characteristics, and further do not include any components to necessarily match the spectral response characteristics of the side sensors with spectral response characteristics of the segments then being evaluated. Such a side sensor arrangement is disclosed in commonly assigned and copending U.S. patent application Ser. No. 679,995, filed Mar. 29, 1991. The afore-referenced patent application also describes various concepts associated with calibration of the spectrophotometer apparatus 200.

The electrical current output signals from the side sensors 292 generated on line pairs 296 are applied as input signals to the linear amplifiers 298. The linear amplifiers 298 can preferably comprise amplifiers having structure and functions similar to the linear amplifiers 288. That is, the linear amplifiers 298 can generate appropriate voltage level output signals on lines 300 proportional to the electrical current input signals on lines 296. As further shown in FIG. 4, appropriate supply voltage can be applied to the linear amplifiers 288 and 298 from the supply voltage circuit 302 by means of lines 304.

Continuing to refer to FIG. 4, the voltage signal outputs form the linear amplifiers 288 are applied as input signals on lines 290 to the multiplexer circuitry 306. The multiplexer circuitry 306 can be conventional in design and comprise a series of one or more conventional multiplexers. The multiplexer circuitry 306 operates so as to time multiplex the output signals from the linear amplifier circuitry onto the conductive paths 308. As further shown in FIG. 4, the multiplexer circuitry 306 will also have an input signal on lines 3.10 from linear amplifier 312. The linear amplifier 312 is utilized to provide an appropriate voltage level signal to the multiplexer circuitry 306 from the battery pack 314. The battery pack 314 will supply appropriate signals as input signals to the linear amplifier 312 on line 316.

Timing for operation of the multiplexer circuitry 306 can be provided by means of clock and similar signals from the processor 318 conductive paths 320. Operation of the processor 318 will be described in greater detail in subsequent paragraphs herein. Again, the structure and function of the multiplexer circuitry 306 is relatively conventional in design. During actual measurements of the reflectance from the object sample 236, the spectrophotometer apparatus 200 will utilize the resultant multiplexed signals on path 308 as sequentially representative reflectance signals from each of the spectrum segments and each of the linear amplifiers 288. In addition, the multiplexed signals will also represent signals sequentially received from each of the optical fiber bundles 254, 256 and 258, representative of reflection signals at the angles 252, 250 and 248, respectively.

The resultant multiplexed signals from the multiplexer circuitry 306 are applied as output signals on the conductive path or paths 308. These signals are further applied as input signals to linear amplifiers 322. The resultant output signals from linear amplifiers 322 are applied as input signals on paths 324 to a relatively conventional analog-to-digital (A/D) convertor circuit 326. The A/D converter 326 comprises a means for converting the analog multiplexed signals on the conductive paths 324 to digital signals for purposes of subsequent processing by the processor 318. The A/D converter 326 can be conventional in design and may be controlled by timing and similar pulse signals applied as input signals on conductive paths 317 from the processor 318 and signals from linear amplifier supply voltage circuit 302 and linear amplifiers 298 on conductive paths 328 and 300, respectively. The signals from the supply voltage 302 on line 328 provide appropriate voltage for operation of the A/D converter 326.

As further illustrated in FIG. 4, the digital output signals from the A/D converter 326 are applied as input signals on paths 330 to the processor 318. The processor 318 is utilized for control of various functions associated with the spectrophotometer apparatus 200, including operation of the motors 260 and 262 previously described with respect to FIG. 3, and corresponding switching of the enabling of optical fiber bundles 254, 256 and 258 in accordance with the invention. Numerous types of conventional and commercially available processors can be employed for the processor 318. An exemplary processor could, for example, comprise the Intel 80C31 8-byte CMOS microcomputer commercially available from the Intel Corporation.

Figure 5:
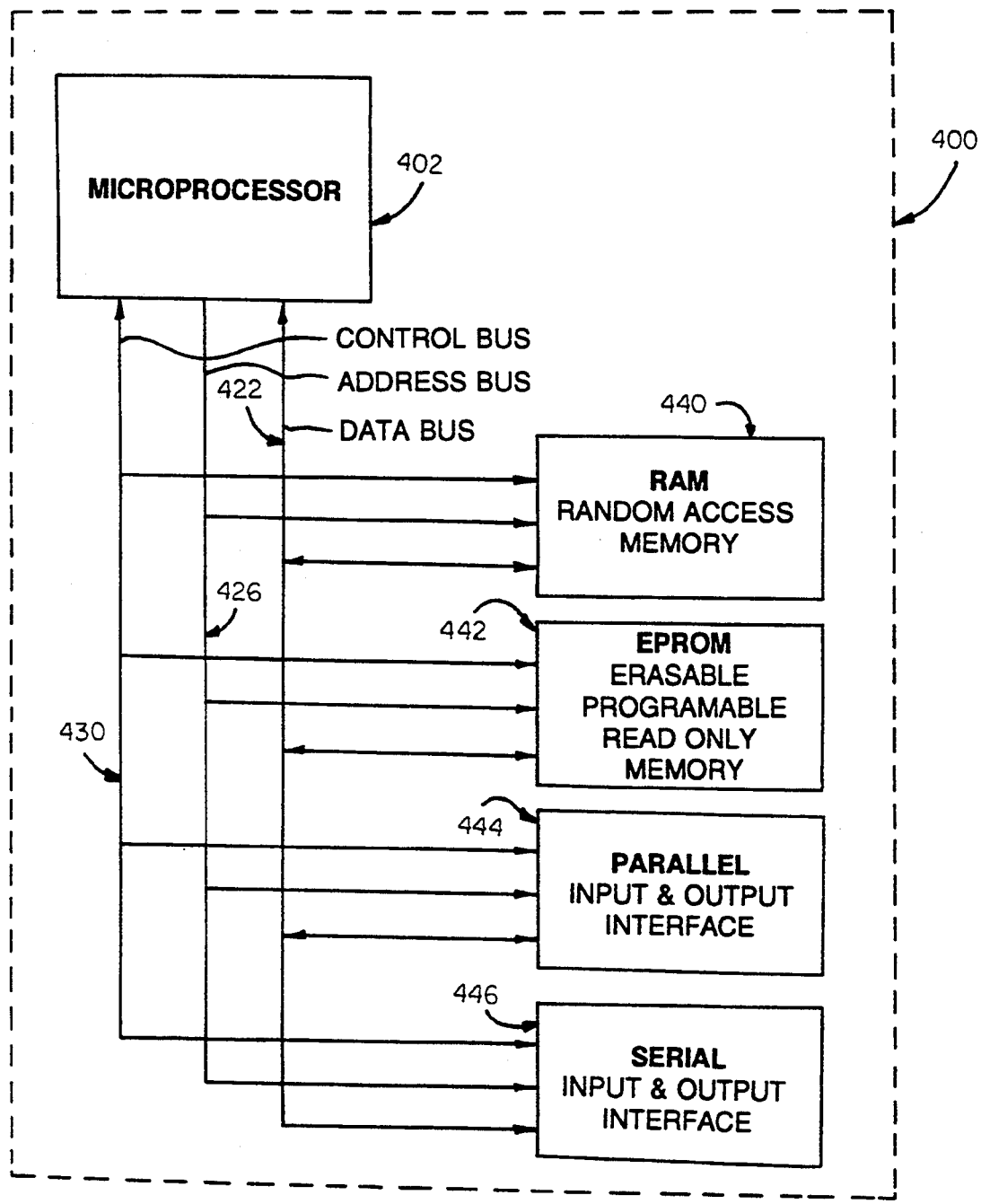
FIG. 5 is a diagram of an exemplary digital processing arrangement.
Figure 6:
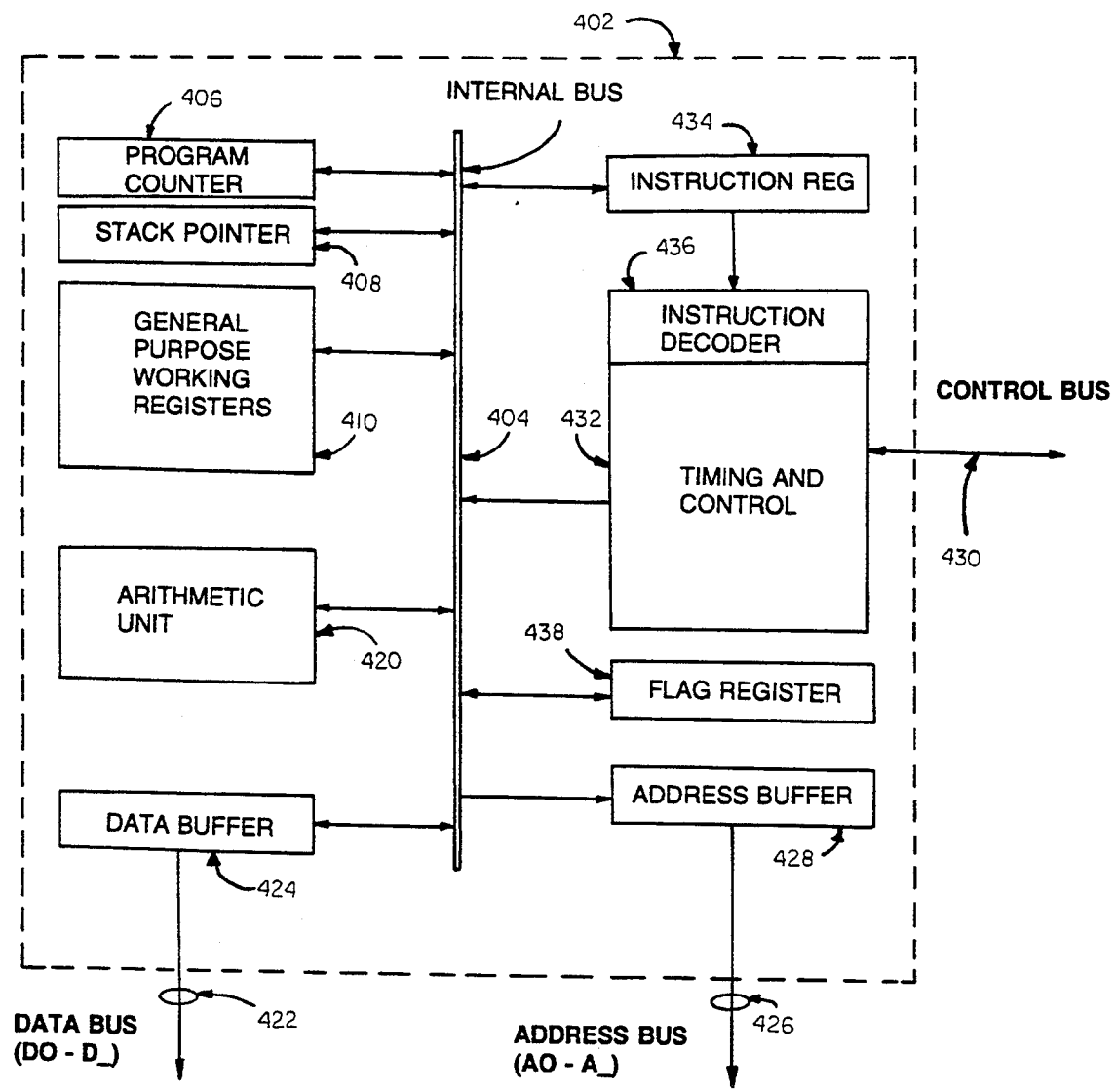
FIG. 6 is a diagram of an exemplary processor configuration.

For purposes of general background, FIGS. 5 and 6 illustrate a general structural diagram of a computer configuration with generalized components. The arrangement shown in FIGS. 5 and 6 does not necessarily correspond specifically to the processor and associated component configuration illustrated in FIG. 4. Instead, FIGS. 5 and 6 are merely for purposes of background description of a generalized form of a programmable device. Referring specifically to FIG. 5, a generalized processing unit 400 is illustrated. As shown therein, the processing unit 400 can comprise a relatively conventional microprocessor 402. As previously described, although various types of well known and commercially available devices can be employed for the processor 402, a typical internal configuration for processor 402 is illustrated in FIG. 6, and a brief and simplistic description thereof will be provided.

Referring specifically to FIG. 6, the processor 402 comprises an internal bus 404 which provides a means for bidirectional communication between conventional circuit components of the processor 402. For example, signals can be transmitted to and received from the program counter 406, which comprise signals representative of the "next" instruction in the computer memory to be executed. Communication can also be provided between the internal bus 404 and processor components such as the stack pointer 408, general purpose registers 410 and arithmetic unit 420. Each of these processor components is well known to those skilled in the art of internal computer system design.

The transmission and reception of data from memories and other components of the processing unit 400 can be provided by the data bus 422 which is connected to the internal bus 404 through a conventional data buffer 424 so as to provide bidirectional communication therewith in the form of multi-digit parallel binary signals. The internal bus 404 is also connected to an address bus 426 through an address buffer 428. The processor 402 can provide, for example, multi-digit parallel binary address signals on the bus 426 for directed communication between the processor 402 and the various memories and other devices having signal communications through the data bus 422.

Conventional system control is provided by interconnection of the control bus 430 to timing and control circuitry 432. Communication signals from the conventional timing and control circuitry 432 can be applied to various components of the processor 402 through the internal bus 404.

The processor 402 also includes other conventional circuit components, including an instruction register 434. The instruction register 434 comprises a register to which the "next" instruction is stored for purposes of decoding an execution. The data within the instruction register 434 is applied to the instruction decoder 436 which comprises conventional circuitry for decoding the instruction data received from the next program location in memory. The processor 402 can also include such conventional components as a flag register 438 utilized for various programming control within the processor 402.

The control bus 430 can be characterized as comprising a series of individual command signal leads. The signal leads can include "transmitted" commands such as "read," "write," memory" and "I/O" commands. In addition, the control bus 430 can be adapted to apply certain "received" commands to the timing and control circuitry 432 Such commands can include "wait, " "reset" and "interrupt" commands. The use of these commands is well known in the field of computer system design. For example, if data is to be read from a certain address location in a memory of the processing unit 400, "enable" signals can be applied to the "read" and "memory" command leads from the timing and control circuitry 432. Correspondingly, the address of the particular memory location to be read can be transmitted on an address bus 426, while the data to be read from the particular memory location will be applied to the processor 402 on data bus 422. Similarly, when data is to be applied to a particular I/O device associated with the processing unit 400, "enable" signals can be applied on the "write" and "I/O" signal command leads from the timing and control circuitry 432. Correspondingly, the address designation of the I/O device can be applied on address bus 426, while the particular data to be transmitted to the I/O device can be applied on data bus 422. Again, the circuitry associated with processor 402, and processor 402 itself are well known in the art.

Returning again to FIG. 5, the processing unit 400 includes memory storage elements such as the random access memory (RAM) 440. The RAM 440 is conventional in design and includes memory locations wherein data may be stored and modified during execution of program sequences. Similarly, for storage of "permanent" data or instructions wherein modifications must be made only occasionally, a conventional erasable-programmable read only memory (EPROM) 442 is also employed. Both the RAM memory 440 and the EPROM memory 442 are interconnected with the processor 402 so as to allow control and address location signals to be applied on the control bus 430 and address bus 426, respectively. In addition, for purposes of reading data from the memories into the processor 402, and for writing data into the memories, bidirectional communication is established between the RAM memory 440, EPROM memory 442 and the processor 402 through data bus 422.

For purposes of intercommunication with external devices, the processing unit 400 can also include a parallel I/O interface module 444 and a serial I/O interface module 446. The parallel interface module 444 provides a means for transmitting and receiving data signals between the processor 402 and external devices which generate and receive signals in parallel format. The serial interface module 446 is utilized to interface with external devices in a serial format.

Like the RAM memory 440 and the EPROM memory 442, the interface modules 444 and 446 are interconnected to the processor 402 through the control bus 430 and address bus 426 for purposes of applying control and address information data signals, respectively, to each of the modules. In addition, the interface modules 444 and 446 are interconnected to the processor 402 through data bus 422 so that data signals are bidirectionally transferrable between the modules 444, 446 and processor 402. It should be emphasized that the general circuitry of the processing unit 400 and the functional operations associated therewith are well known in the field of computer system design.

The aforedescribed processor configuration as illustrated in FIGS. 5 and 6 is merely exemplary of certain of the general concepts associated with processor and associated component design. In the particular embodiment illustrated in FIG. 4, the processor is illustrated as a separate processing unit 318 independent of the memory and similar elements. As further shown in FIG. 4, the processor 318 can provide control signals to both the supply voltage circuitry 302 and lamp control circuitry 332 via transmission paths 334 and 336, respectively. Control signals can also be applied from the processor 318 to the power supply circuit 338 via path 340. In addition, various control signals can be applied to conventional reset circuitry 342 from the processor 318 and power supply circuit 338 as illustrated in FIG. 4. Although FIG. 4 further illustrates other interconnections among components such as the power supply circuit 338 and the reset circuit 342, the structure and function of such interconnections will be apparent from the illustration of FIG. 4 and other detailed descriptions set forth herein.

The spectrophotometer apparatus 200 can also comprise a conventional address decoder 344 interconnected to the address bus of the bus configuration 346 for the processor 318. The address decoder 344 is utilized to decode the address range for the various devices associated with the bus configuration 346. Such an address decoder configuration is convention in design.

The apparatus 200 can also include a conventional EPROM 348 which can comprise, for example, a CMOS 512K EPROM. A serial EEPROM 319 can also be provided. In addition, the spectrophotometer apparatus 200 can also comprise a random access memory (RAM) 350. The RAM 350 can, for example, comprise an 8192 byte static random access memory.

As previously described, the spectrophotometer apparatus 200 can also include a series of keys 216. These keys 216 provide a means for manual input of data by the spectrophotometer operator. Still further, the apparatus 200 further includes the display 212 for purposes of providing data display to the operator. In association with the aforedescribed components which are directly or indirectly connected to the bus configuration 346 of the processor 318, conventional latching circuitry 352 is also employed for purposes of latching data applied to and from the bus configuration 346.

As further shown in FIG. 4, the processor 318 is interconnected to a conventional RS232 I/O interface circuit 354. The interface circuit 354 provides an interface to an external computer or printer device 356, for purposes of transmitting and receiving data to and from the interface device, respectively. Control signals from the processor 318 to the interface 354 can be applied via path 358. Correspondingly, data from the processor 318 can be applied as input data through the interface 354 via transmission path 360. Correspondingly, data from the computer or printer device 356 can be applied through the interface 354 and input to the processor 318 by means of transmission path 362.

The circuit configuration 280 also includes a set of read switches 364 having signals which are applied as input signals to the processor 318 by means of transmission paths 366. Further, the circuit configuration 280 also includes the power switch 220 and A/C adaptor 210. Still further, although not specifically shown in FIG. 4, the processor 318 would include control signals which can be applied as input signals to the motors 260 and 262 previously described with respect to FIG. 3. The control of the motors 260 and 262 would occur for purposes of controlling the enabling and disabling of reception of light through the optical fiber bundles 254, 256 and 258.

The foregoing provides a brief description of various of the components of the circuit configuration 280 of the spectrophotometer apparatus 200. Many of these components are also utilized in various other types of color measurement apparatus. For example, a detailed description of similar components for use in a densitometer are described in detail in the commonly assigned and currently pending U.S. patent application Ser. No. 480,331 filed Feb. 13, 1990, which is a continuation of commonly assigned U.S. patent application Ser. No. 309,342 filed Feb. 10, 1989, and now abandoned. Concepts associated with the use of a color measurement device and an interface for communication with external devices are disclosed in the commonly assigned Peterson et al U.S. Pat. No. 4,591,978, issued May 27, 1986.

In brief summary, the apparatus 200 is adapted to operate as an automated instrument for providing a spectral reflectance analysis of object samples. When the object sample 236 is positioned appropriately relative to the spectrophotometer apparatus 200, light from the source unit 238 is projected onto the surface of the sample 236, and reflected light rays 240, 242 and 244 are received by the optical fiber bundles 254, 256 and 258, respectively. A separate optical fiber bundle is provided for each of the angles 248, 250 and 252. The light rays passing through the optical fiber bundles 254, 256 and 258 are applied to a single array of filters and corresponding photocells 284. Each of the filters will substantially pass the reflected light only within the bandwidth corresponding to the particular segment. Electrical current signals generated from the photocells of the configuration 284 are applied to linear amplifiers 288, and voltage output signals are generated therefrom.

The voltage output signals from the linear amplifiers 288 are applied as input signals to the multiplexers 306. The multiplexers 306 provide time multiplexed signals which are applied as input signals to the A/D convertor 326 through the linear amplifiers 322. The converter 326 converts the analog signals to appropriate digital signals, and applies the same to the processor 318. The processor 318 can be utilized to perform appropriate computations and measurements of the digital signals from paths 330 so as to generate data indicative of the spectral reflectance characteristics of the object sample 236 for each of the spectral segments and for each of the angles 248, 250 and 252. As desired, this data can be visually displayed to an operator through the display 212. Corresponding, such data can be applied to the external devices 356 through the interface 354. Control of the processor 318 can be provided, at least in part, through operator input from the keys 216. The general operation of spectrophotometers, given spectral data from a series of segments, is relatively well known in the art.

Although the primary data provided to the processor 318 is representative of spectral reflectance data at various segments across the visible light spectrum, the processor 318 can be utilized in a conventional manner to convert the data into other formats. For example, the spectral reflectance data can be utilized to generate CIE L*a*b* and L*C*h° color values. The processor 318 can also be utilized to store data within the memory 350. The data stored can include not only color measurements, but can also include difference measurements for purposes of comparison to various standards.

Of primary importance, however, in accordance with the invention, the circuit configuration 280 and the electromechanical configuration of the spectrophotometer apparatus 200 as previously described with respect to FIG. 3 provide for the measurement of spectral reflectance of object samples 236 by illumination at a particular fixed angle, while receiving light at three fixed angles different from the illumination angle. In accordance with the switching arrangement as described with respect to FIG. 3, reflectance is measured at each of the angles 248, 250 and 252 by sequentially switching combinations of two of the angles to a "disabled" state, and receiving reflected light rays through the optical fiber bundle corresponding to the remaining angle. As further described in detail with respect to FIG. 3, such optical switching is achieved through the use of an electromechanical shutter arrangement. As described with respect to FIG. 4, the reflected light rays projecting through the optical fiber bundles 254, 256 and 258 are transferred to a single array of integral interference-filter/photodiode devices corresponding to the filtered photocells 284. The filtered photocells 284 can be characterized as modulating the reflected light rays for purposes of determination of spectral characteristics.

Figure 7:
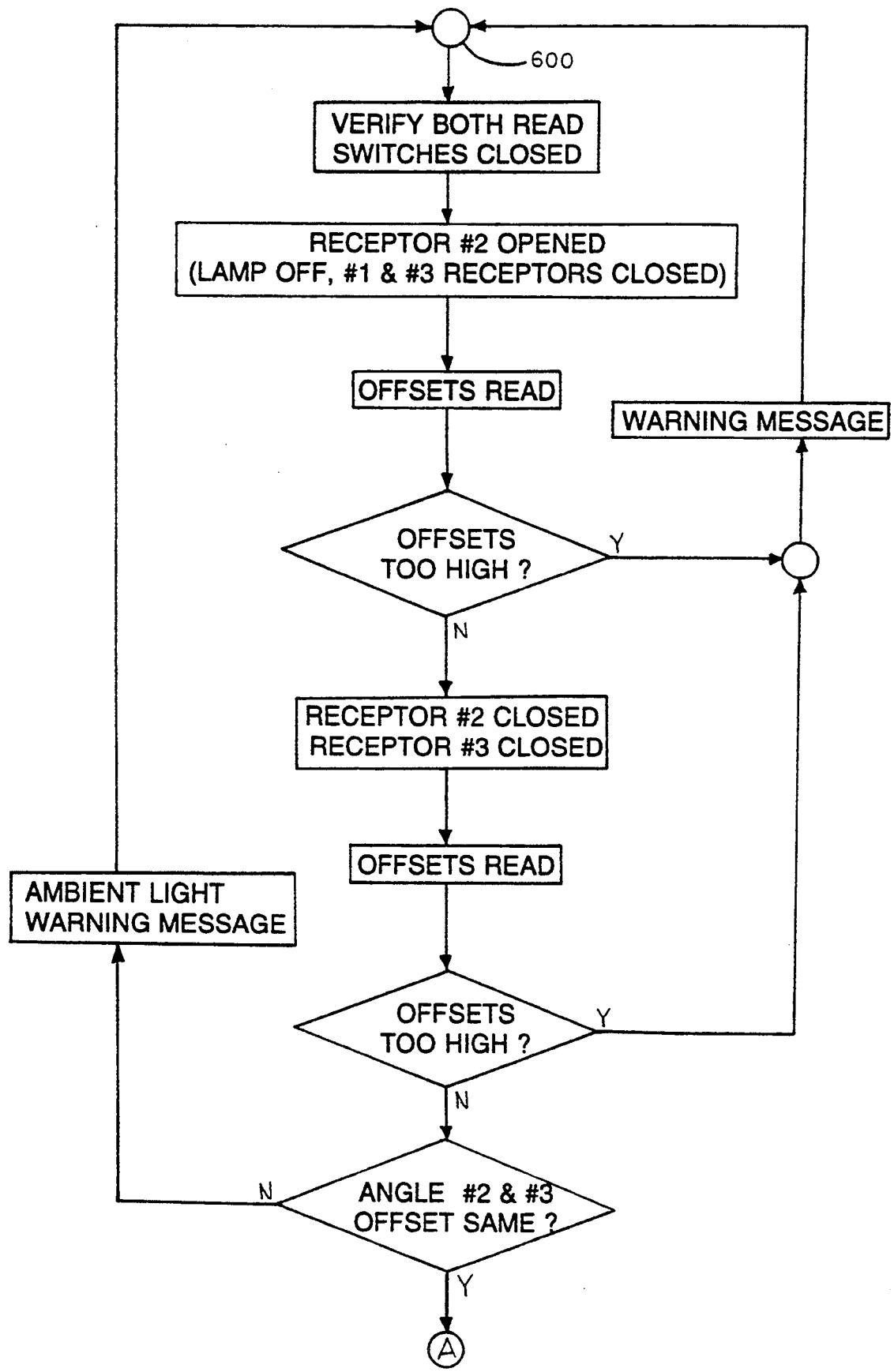
FIG. 7 represents a functional sequence diagram for performance of certain procedures of the spectrophotometer apparatus in accordance with the invention.
Figure 7A:
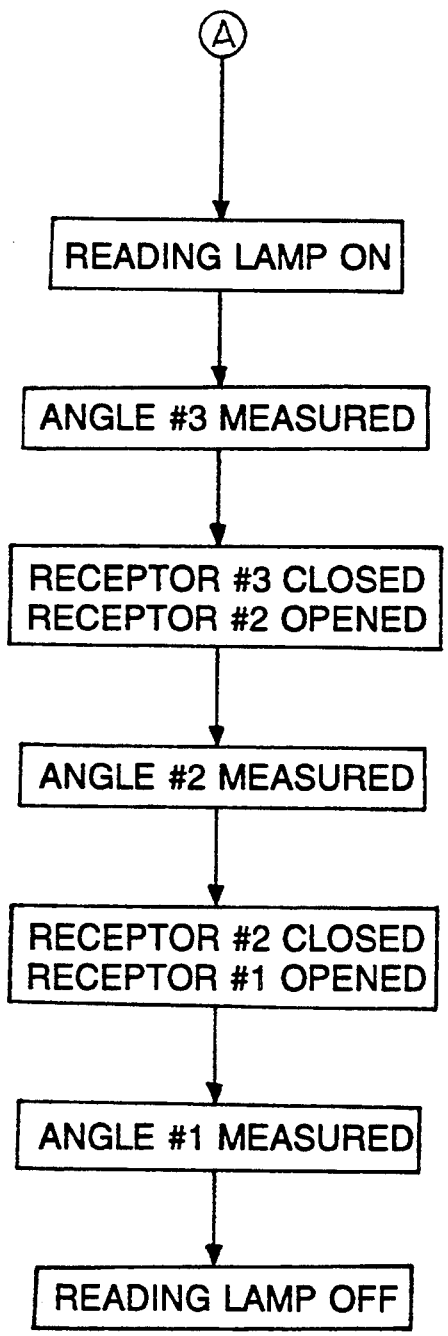

For purposes of efficiency of operation, various functions associated with the spectrophotometer apparatus 200 can be achieved through the use of computer programs operating within the processor 318. A functional sequence diagram associated with the reception of light rays and optical switching is illustrated in FIG. 7. With specific reference to FIG. 7, operation of the computer programs within the processor 318 can commence at functional location 600. Thereafter, a verification is made that the read switches 364 are in a closed state. For purposes of further description with respect to the functional sequence diagram of FIG. 7, references in FIG. 7 to the "receptor" numbers 1, 2 and 3 correspond to the shuttering of the optical fiber bundles 248, 250 and 252. That is, a receptor characterized as being in an open state corresponds to the electromechanical shuttering arrangement having a positional relationship with respect to the corresponding optical fiber bundle such that light can be received through the optical fiber bundle.

With the foregoing in mind, a determination is first made to assure that the electromechanical shuttering arrangement is operating properly and the object sample 236 is appropriately positioned so that excessive "light leak" is not occurring. To ensure that the same does not present a problem, the optical fiber bundle corresponding to receptor number 2 is opened so as to receive reflected light rays. The light source unit 226 is maintained in an "off" state, and the optical fiber bundles corresponding to receptor numbers 1 and 3 are in a closed position through the use of the electromechanical shuttering arrangement. Light readings (corresponding to "offsets" as illustrated in FIG. 7) are then made, and a determination is further made as to the intensity of such received reflected light rays corresponding to the offsets. A further determination is then made as to whether such offsets exceed a predetermined threshold. If so, a warning message is generated by the processor 318 and applied to the display 212 for viewing by the operator.

If the offsets do not exceed a predetermined threshold, a further test is made whereby receptor number 2 is electromechanically shuttered, and the optical fiber bundle corresponding to receptor number 3 is opened so as to receive light rays. Optical measurements are then again made, and a determination is further made as to whether the "offset" measurements exceed a predetermined threshold. If so, a warning message is applied to the display 212 for the operator.

If the offsets do not exceed the predetermined threshold, it can be assumed that "light leak" does not present a problem, and a determination is then made as to any potential problems with respect to "flatness." That is, a determination is made as to whether the offsets corresponding to angle numbers 2 and 3 are the same. If they are not the same, a warning message regarding ambient light is generated and applied to the display 212.

Assuming that the offsets are substantially the same, the light source unit 212 is enabled, so that the lamp projects light onto the object sample 236. The reflected light rays associated with angle number 3 are then measured. It should be remembered that during the aforedescribed testing operations, receptor number 3 was positioned in an open state, while the electromechanical shuttering maintained receptor numbers 1 and 2 in a closed state. Following the measurement of reflected light rays associated with angle number 3, the optical fiber bundle corresponding to receptor number 3 is closed and the optical fiber bundle associated with receptor number 2 is opened. Angle number 2 is then measured with respect to the reflected light rays.

Following the measurement of angle number 2, the optical fiber bundle corresponding to receptor number 2 is closed while the optical fiber bundle corresponding to receptor number 1 is opened. The reflected light rays associated with angle number 1 as received through the receptor number 1 are then measured. The foregoing provides a complete sequence of measurements through all three angles of the optical measurement device. Following this measurement, the light source unit 226 is disabled, so that the lamp is set to an "off" position. The spectral reflectance measurements associated with each of the angles can be combined in an appropriate manner so as to provide for a "quality of color" measurement with respect to the object sample 236. Any of numerous combinations can be made with respect to the reflected light rays received at each of the three angles. For example, the combining of reflected light rays is described in detail in the Alman and Steenhoek patents previously described herein.

In summary, the spectrophotomer apparatus 200 in accordance with the invention provides for three angles of "pickup" of reflected light rays, with the utilization of three separate optical fiber bundles. The optical fiber bundles are electromechanically shuttered in sequence, so that reflected light rays are received from only one of the optical fiber bundles at any given time. Further in accordance with the invention, only a single light source is utilized, and only a single array of photosensitive detectors (corresponding to the filtered photocells 284) is .required. Still further, the entire unit, including all battery sources, are contained within a single unitary structure, comprising a hand held and extremely portable unit.

Also of primary importance, the use of the single light source and the single array of filtered photocells provides a significant advantage with respect to reduction of cost. In addition, with the single array of filtered photocells, compensation is not required among multiple detectors. Still further, the use of the single array of photocells and the single light source provides a significant advantage with respect to reduction in size and weight, especially relative to several known systems which employ three detectors. Still further, the spectrophotometer apparatus 200 in accordance with the invention allows for the object sample under test 236 to be stationary when reflectance measurements are achieved. Finally, the apparatus in accordance with the invention provides for detection of "light leak" and flatness.

It should be emphasized, however, that the principles of these spectrophotometer apparatus comprising multi-angular measurements are not limited to the specific apparatus described herein. In fact, the procedures associated with the multi-angular measurements can be employed with apparatus other than spectrophotometers. Still further, the features of the multi-angular spectrophotometer in accordance with the invention are not in any manner necessarily limited to any specific angular measurements, specific number of spectral segments or the like. A different number of segments and filters having various band widths can be employed without departing from the novel concepts of the invention, and various angles can be utilized for purposes of reflectance measurements. It will be further apparent to those skilled in the art that additional modifications and variations of the above-described illustrative embodiment of the invention may be effected without departing from the spirit and scope of the novel concepts of the invention.

The embodiments of the invention in Which an exclusive property or privilege is claimed or defined as follows:

1. An apparatus adapted for measuring color characteristics of a colored surface, said apparatus comprising:
    a light source for projecting light toward said colored surface at at least one angle of illumination relative to said surface;
    light receivers for receiving light rays reflected from said colored surface at a plurality of reflection angles relative to said surface;
    a detector connected to said light receivers for detecting said light rays reflected from said colored surface and for generating electrical signals representative of spectral characteristics of said surface, for each of a series of spectral segments across the visible light spectrum;
    a processor connected to said detector and responsive to said electrical signals for generating data representative of said spectral characteristics; and
    said apparatus further comprises switching means positioned adjacent said light receivers for periodically inhibiting said light rays reflected from said colored surface from being received by all but one of said light receivers.

2. An apparatus in accordance with claim 1 characterized in that said detector comprises only a single array of filtered photodetectors, each of said filtered photodetectors comprising a filter and a photodetector, wherein each filter associated with a corresponding photodetector comprises a spectral response characteristic different from filters associated with all other photodetectors of said array.

3. An apparatus in accordance with claim 1 characterized in that said detector comprises a single array of filtered photodetectors for detecting said light rays reflected from said colored surface at each angle of said plurality of reflection angles.

4. An apparatus in accordance with claim 1 characterized in that said light receivers comprise a plurality of optical fiber bundles.

5. An apparatus in accordance with claim 4 characterized in that said detector comprises an array of filtered photodetectors, and light rays reflected from said colored surface and received through all of said optical fiber bundles are applied to said array of filtered photodetectors.

6. An apparatus in accordance with claim 1 characterized in that said light source projects light toward said colored surface only at one angle of illumination relative to said surface.

7. An apparatus in accordance with claim 1 characterized in that said light receivers receive said light rays reflected from said colored surface at three reflection angles relative to said surface.

8. An apparatus in accordance with claim 7 characterized in that said three reflection angles are substantially equal to 25°, 45°, and 110° relative to a specular angle.

9. An apparatus in accordance with claim 1 characterized in that said switching means comprises:
    shutter means positioned adjacent said light receivers for periodically and mechanically inhibiting said light rays reflected from said colored surface from being received by all but one of said light receivers, said shutter means being movable among open and closed positions; and
    motive means coupled to said shutter means and responsive to said processor for moving said shutter means among said open and closed positions.

10. An apparatus in accordance with claim characterized in that said shutter means comprises a pair of optical shutter devices, each of said shutter devices comprising:
    a pair of optical shutters positioned substantially at a 90° angle relative to each other;
    a rotatable portion connected to said pair of optical shutters; and
    an arm follower connected to said rotatable portion and coupled to said motive means.

11. An apparatus in accordance with claim 10 characterized in that said motive means comprises a pair of motors, each of said motors being operably coupled to a different one of said optical shutter devices.

12. An apparatus in accordance with claim 9 characterized in that:
    said light receivers comprise a plurality of optical fiber bundles;
    said shutter means comprises a pair of optical shutter devices, each of said shutter devices comprising a pair of optical shutters;
    a first one of a first pair of said pairs of optical shutters is responsive to said motive means to periodically inhibit said light rays reflected from said colored surface from being received by a first one of said plurality of optical fiber bundles;
    a second one of said first pair of said pairs of optical shutters is responsive to said motive means to periodically inhibit said light rays reflected from said colored surface from being received by a second one of said plurality of optical fiber bundles;

a first one of a second pair of said pairs of optical shutters is responsive to said motive means to periodically inhibit said light rays reflected from said colored surface from being received by said second one of said plurality of optical fiber bundles; and a second one of said second pair of said pairs of optical shutters is responsive to said motive means to periodically inhibit said light rays reflected from said colored surface from being received by a third one of said plurality of optical fiber bundles.

13. An apparatus in accordance with claim 1 characterized in that said apparatus is enclosed in a hand-held and portable structure.

14. An apparatus in accordance with claim 1 characterized in that said apparatus comprises means for testing for light leak of said apparatus by detecting light rays reflected from said colored surface in the absence of illumination by said light source and while said all but one of said light receivers is inhibited from receiving said light rays.

15. A spectrophotometer adapted for measuring color characteristics of a colored surface, said spectrophotometer comprising:

a light source for projecting light toward said colored surface at at least one angle of illumination relative to said surface;

a plurality of optical fiber bundles for receiving light rays reflected from said colored surface at a plurality of reflection angles relative to said surface;

a single array of filtered photodetectors for detecting said light rays reflected from said colored surface and received through said plurality of optical fiber bundles, for generating electrical signals representative of spectral characteristics of said surface, said array having a plurality of filter and photodetector sets, with each filter having a spectral response characteristic different from other filters of said array;

a processor connected to said array and responsive to said electrical signals for generating data representative of said spectral characteristics; and switching devices positioned adjacent to said plurality of optical fiber bundles for inhibiting, at any given time, all but one of said plurality of optical fiber bundles from receiving said light rays reflected from said colored surface.

16. A spectrophotometer in accordance with claim 15 characterized in that:

said light source projects light toward said colored surface only at one angle of illumination relative to said surface; and said plurality of optical fiber bundles and said plurality of reflection angles are each three in number.

17. A method for measuring color characteristics of a colored surface, said method comprising the steps of:

projecting light toward said colored surface at a single angle of illumination relative to said surface;

receiving light rays reflected from said colored surface through a plurality of optical fiber bundles at a plurality of reflection angles relative to said surface;

periodically inhibiting said light rays reflected from said colored surface from being received by all but one of said plurality of optical fiber bundles;

detecting said light rays reflected from said colored surface after said light rays have been received through certain of said optical fiber bundles, and generating electrical signals representative of spectral characteristics of said surface, for each of a series of spectral segments across the visible light spectrum; and generating data representative of said spectral characteristics in response to said electrical signals.

18. A method in accordance with claim characterized in that said method further comprises the steps of:

maintaining said light source in an off state;

maintaining all but a first one of said optical fiber bundles in a closed position, whereby optical fiber bundles in a closed position are inhibited from receiving any light rays reflected from said colored surface;

maintaining said first one of said optical fiber bundles in an open position;

measuring intensity of light rays reflected from said colored surface and received through said first one of said optical fiber bundles; and determining whether said measured intensity exceeds a predetermined threshold.

19. A method in accordance with claim 18 characterized in that said method further comprises the steps of:

maintaining all but a second one of said optical fiber bundles in a closed position;

maintaining said second one of said optical fiber bundles in an open position;

measuring intensity of light rays reflected from said colored surface and received through said second one of said optical fiber bundles; and determining equivalence or an absence of equivalence between said measured intensities of light rays received through said first one and said second one of said optical fiber bundles.

* * * * *

UNITED STATES PATENT AND TRADEMARK OFFICE
CERTIFICATE OF CORRECTION

PATENT NO. :   5,387,977
DATED      :   February 7, 1995
INVENTOR(S):   Bernard J. Berg et al.

It is certified that error appears in the above-identified patent and that said Letters Patent is hereby corrected as shown below:

Column 30, claim 10, line 41:
    after "claim" insert --9--.

Signed and Sealed this

Twenty-seventh Day of June, 1995

Attest:

BRUCE LEHMAN

Attesting Officer       Commissioner of Patents and Trademarks